US012721540B2

(12) United States Patent
Muse et al.

(10) Patent No.: US 12,721,540 B2
(45) Date of Patent: Sep. 1, 2026

(54) MACHINE LEARNING-BASED SYSTEMS AND METHODS FOR BREATH MONITORING AND ASSISTANCE OF A PATIENT

(71) Applicant: UnitedHealth Group Incorporated, Minnetonka, MN (US)

(72) Inventors: Jon Kevin Muse, Thompsons Station, TN (US); Marilyn L. Gordon, Cherry Hill, NJ (US); Komal Khatri, Cedar Park, TX (US); Gregory J. Boss, Saginaw, MI (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 1264 days.

(21) Appl. No.: 17/521,319

(22) Filed: Nov. 8, 2021

(65) Prior Publication Data

US 2023/0146449 A1 May 11, 2023

(51) Int. Cl.

*A61B 5/08* (2006.01)
*A61B 5/00* (2006.01)
*A61N 1/36* (2006.01)

(52) U.S. Cl.

CPC .......... *A61B 5/0816* (2013.01); *A61B 5/4836* (2013.01); *A61B 5/7246* (2013.01);
(Continued)

(58) Field of Classification Search

None
See application file for complete search history.

(56) References Cited

U.S. PATENT DOCUMENTS 5,485,854 A * 1/1996 Hollister .......... A61B 5/150351 600/576
6,654,642 B2 11/2003 North et al.
(Continued)

FOREIGN PATENT DOCUMENTS

WO 2021/092533 A1 5/2021

OTHER PUBLICATIONS

"Atelectasis - Symptoms and Causes," Mayo Clinic, Sep. 5, 2018, (4 pages), (article, online), [Retrieved from the Internet Feb. 17, 2022] <URL: https://www.mayoclinic.org/diseases-conditions/atelectasis/symptoms-causes/syc-20369684?p=1>.
(Continued)

*Primary Examiner* — Benjamin J Klein
*Assistant Examiner* — Willow Grace Welch
(74) *Attorney, Agent, or Firm* — Alston & Bird LLP

(57) ABSTRACT

Apparatus, systems, and methods for real time monitoring of a patient's breathing utilizing automatically controlled devices and machine learning based techniques to determine a full breath of a patient and to identify splinting points, and to thereby transmit stimulation signals to the patient so as to assist the patient breathe through splinting points. In some embodiments, a wearable breathing monitoring device comprising of one or more sensors configured to monitor the user's breathing and a stimulator apparatus comprising one or more transmitters configured to transmit stimulation signals to the patient at a time corresponding to a detected splinting point is provided. The stimulator apparatus is configured to apply electrical pulses according to a stimulation schedule via the transmitters to target nerves of the user's body.

20 Claims, 11 Drawing Sheets

(52) U.S. Cl.
CPC .......... *A61B 5/7264* (2013.01); *A61N 1/3601* (2013.01); *A61N 1/3603* (2017.08); *A61N 1/36031* (2017.08); *A61N 1/3611* (2013.01); *A61N 1/36139* (2013.01); *A61N 1/3615* (2013.01); *A61N 1/36167* (2013.01); *A61N 1/36175* (2013.01)

(56) References Cited

U.S. PATENT DOCUMENTS

| | | | | |
|---|---|---|---|---|
| 2005/0061315 | A1* | 3/2005 | Lee | A61B 5/4818 128/204.23 |
| 2010/0042137 | A1 | 2/2010 | Oronsky et al. | |
| 2012/0035680 | A1* | 2/2012 | Napadow | A61B 5/113 607/45 |
| 2013/0013026 | A1* | 1/2013 | Hoyer | A61H 3/00 607/49 |
| 2015/0045848 | A1* | 2/2015 | Cho | A61B 5/0816 607/18 |
| 2016/0346530 | A1 | 12/2016 | Jeffery et al. | |
| 2018/0184963 | A1 | 7/2018 | Levanon | |
| 2019/0151604 | A1 | 5/2019 | Harper et al. | |
| 2019/0175908 | A1 | 6/2019 | Thakkar et al. | |
| 2019/0374772 | A1 | 12/2019 | Baik | |
| 2020/0163627 | A1* | 5/2020 | Sayadi | G01G 21/02 |

OTHER PUBLICATIONS

"Atelectasis," Wikipedia, Nov. 14, 2021, (6 pages), (online), [Retrieved from the Internet Feb. 17, 2022] <URL: https://en.wikipedia.org/wiki/Atelectasis#:~: text=The%20most%20common%20cause%20is,also%20at%20an%20increased%20risk>.

Dadonaite, Bernadeta et al. "Pneumonia," Our World In Data, Nov. 2019, (19 pages), (article, online), [Retrieved from the Internet Feb. 17, 2022] <URL: https://ourworldindata.org/pneumonia>.

Johnson, Mark I. "Resolving Long-Standing Uncertainty about the Clinical Efficacy of Transcutaneous Electrical Nerve Stimulation (TENS) to Relieve Pain: A Comprehensive Review of Factors Influencing Outcome," Medicina, vol. 57, No. 4, Apr. 14, 2021, pp. 1-35, available online: https://doi.org/10.3390/medicina57040378.

* cited by examiner

MACHINE LEARNING-BASED SYSTEMS AND METHODS FOR BREATH MONITORING AND ASSISTANCE OF A PATIENT

BACKGROUND

Individuals that experience pain during an inspiration portion of a breath may—either knowingly or unknowingly—shorten their breath in a breathing pattern known as "splinting" to avoid painful portions of a full breath cycle. Splinting is common in post-operative patients and those experiencing conditions such as pleurisy or atelectasis. When splinting occurs over an extended period of time, long-term changes in the patients' breathing patterns may develop, and those long-term patterns may be difficult to reverse even after the breathing-related pain subsides.

Accordingly, a need exists for systems and methods that effectively and efficiently assist patients in overcoming splinting occurrences.

BRIEF SUMMARY

Embodiments as described herein provide systems, apparatus, and methods for monitoring an individual's breath and providing assistance. For detecting splinting and corresponding splinting points, various embodiments process captured breathing pattern sensory data for a monitored individual and generate breathing waveform data, based at least in part on the breathing sensory data, that is then compared with one or more expected breathing waveform data for the monitored individual so as identify locations in the breathing waveform data that are indicative of splinting. For assisting a patient breathe through a splinting point in inspiration, various embodiments transmit a stimulation signal to the monitored individual corresponding to a detected splinting point so as to provide a therapeutic reflexology nerve stimulation and/or serve as a distraction for the monitored individual to breathe through pain.

In accordance with one aspect, a method is provided. In one embodiment, the method comprises: receiving breathing pattern sensory data generated based at least in part on output of a breathing sensor monitoring a monitored individual's breathing; generating breathing waveform data reflecting a breathing cycle of inspiration and expiration of the monitored individual based at least in part on the breathing pattern sensory data for the monitored individual; determining one or more splinting occurrences reflected within the breathing waveform data; mapping a stimulation schedule to the breathing waveform data, wherein the stimulation schedule defines one or more stimulation triggers reflected within the breathing waveform data and detectable within the breathing pattern sensory data for stimulating nerves of the monitored individual; and in response to detecting a stimulation trigger of the one or more stimulation triggers within the breathing pattern sensory data, causing a stimulator in contact with the monitored individual to emit a stimulation signal to the monitored individual, wherein the stimulation signal is characterized by stimulation parameters.

In accordance with another aspect, a computer program product is provided. The computer program product may comprise at least one computer-readable storage medium having computer-readable program code portions stored therein, the computer-readable program code portions comprising executable portions configured to: receive breathing pattern sensory data generated based at least in part on output of a breathing sensor monitoring a monitored individual's breathing; generate breathing waveform data reflecting a breathing cycle of inspiration and expiration of the monitored individual based at least in part on the breathing pattern sensory data for the monitored individual; determine one or more splinting occurrences reflected within the breathing waveform data; map a stimulation schedule to the breathing waveform data, wherein the stimulation schedule defines one or more stimulation triggers reflected within the breathing waveform data and detectable within the breathing pattern sensory data for stimulating nerves of the monitored individual; and in response to detecting a stimulation trigger of the one or more stimulation triggers within the breathing pattern sensory data, cause a stimulator in contact with the monitored individual to emit a stimulation signal to the monitored individual, wherein the stimulation signal is characterized by stimulation parameters.

In accordance with yet another aspect, an apparatus comprising at least one processor and at least one memory including computer program code is provided. In one embodiment, the at least one memory and the computer program code may be configured to, with the processor, cause the apparatus to: receive breathing pattern sensory data generated based at least in part on output of a breathing sensor monitoring a monitored individual's breathing; generate breathing waveform data reflecting a breathing cycle of inspiration and expiration of the monitored individual based at least in part on the breathing pattern sensory data for the monitored individual; determine one or more splinting occurrences reflected within the breathing waveform data; map a stimulation schedule to the breathing waveform data, wherein the stimulation schedule defines one or more stimulation triggers reflected within the breathing waveform data and detectable within the breathing pattern sensory data for stimulating nerves of the monitored individual; and in response to detecting a stimulation trigger of the one or more stimulation triggers within the breathing pattern sensory data, cause a stimulator in contact with the monitored individual to emit a stimulation signal to the monitored individual, wherein the stimulation signal is characterized by stimulation parameters.

BRIEF DESCRIPTION OF THE SEVERAL VIEWS OF THE DRAWINGS

Reference will now be made to the accompanying drawings, which are not necessarily drawn to scale, and wherein.

DETAILED DESCRIPTION

Figure 1:
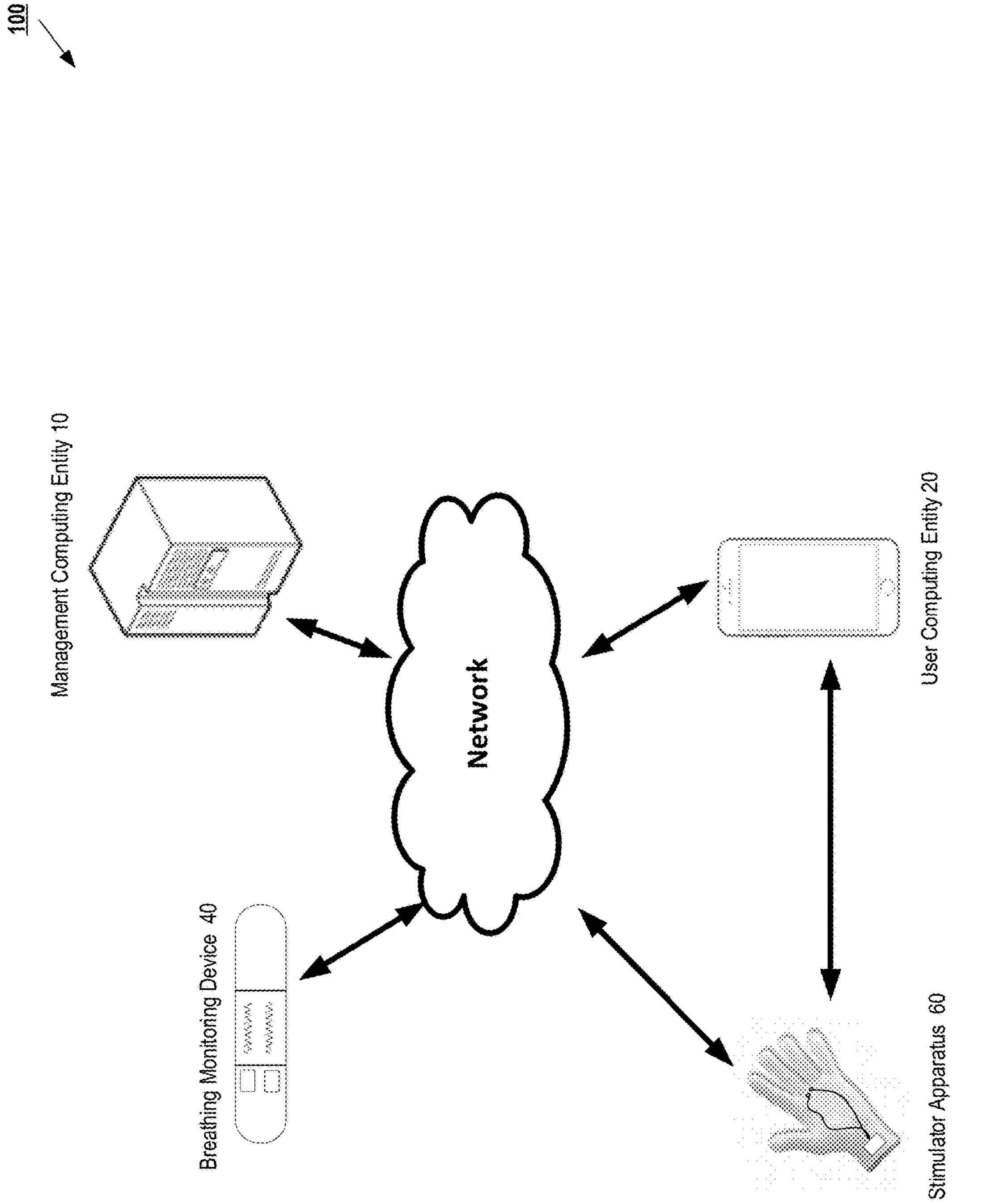
FIG. 1 is an exemplary overview of a system architecture that can be used to practice various embodiments.

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

Overview

Various embodiments provide apparatus, systems, computer program products, and/or the like for monitoring a patient's breathing; capturing breathing data reflecting a breathing cycle of inspiration and expiration of the patient; detecting splinting points in the inspiration of the patient, reflected within the breathing waveform data; and transmitting stimulation signals to the patient at a time corresponding to a detected splinting point.

Splinting points in a patient's breathing are determined by receiving breathing pattern sensory data generated based at least in part on output of a breathing sensor (breathing monitoring device) monitoring an individual's breathing and generating breathing waveform data reflecting a breathing cycle of inspiration and expiration of the monitored individual based at least in part on the breathing pattern sensory data for the monitored individual. The breathing monitoring device is attached to a patient's chest, or otherwise is provided to monitor movements of the patient's chest that are indicative of the patient's breathing. If the patient hesitates, pauses, or shortens his/her breath, data generated by the breathing monitoring device reflects this aspect of the patient's breathing, so as to identify splinting points within the patient's cycle of breathing. The breathing waveform data is then processed/analyzed (e.g., utilizing a machine learning model) to determine whether splinting is reflected within the breathing waveform data. If splinting is detected, the system uses a stimulation device (alternatively referred to as stimulator apparatus) to stimulate the patient's nerves (e.g., using electrical stimulation) at moments of the patient's breathing cycle that correlate to splinting instances, so as to provide nervous-system stimulation in an effort to help the patient overcome splinting to complete the patient's full breath. The stimulation is provided according to a stimulation schedule that is mapped to the breathing waveform data. The stimulation schedule may define one or more stimulation triggers reflected within the breathing waveform data and detectable within the breathing pattern sensory data for stimulating nerves of the monitored individual. In response to detecting a stimulation trigger of the one or more stimulation triggers within the breathing pattern sensory data, a stimulator in contact with the monitored individual is caused to emit a stimulation signal to the monitored individual to assist the patient in breathing through the detected splinting points.

Technical Problem

Treatments for breathing-related patient ailments, such as atelectasis or pleurisy (or for post-operative recovery relating to lung-related surgery) generally aim to allow a patient to take a full breath with minimal to no pain, while also avoiding long-term damage to the patient's lungs. However, existing technology is incapable of identifying, estimating, or otherwise determining what constitutes a "full" breath for the patient, so that treatment can be tailored to assist the patient in overcoming any difficulties in breathing. Instead, existing treatments rely on the professional judgment of care providers based on extremely limited insights into the patient's breathing patterns—insights that are typically garnered during unrealistic treatment settings in which the patient is consciously focusing on his/her breathing and therefore any insight obtained by the care provider is not representative of day-to-day breathing patterns of the patient that could otherwise provide information about what constitutes a full breath of the patient and/or that could otherwise provide information about how, when, and/or why the patient is suffering from limited breathing capacity.

Technical Solution

To address the foregoing technical challenges, embodiments as discussed herein utilize automatically controlled devices and machine learning based techniques to determine a full breath of a patient and/or to identify points of splinting while the patient is breathing (e.g., during a therapy session) by monitoring the patient's breathing in real time, using machine learning to determine an estimated wave-form reflecting the patient's full breath (both inspiration and expiration), using machine learning to predict/detect splinting points and providing therapeutic reflexology nerve stimulation during inspiration of the patient, where the stimulation is provided at a moment in the inspiration corresponding to a predicted splinting point. Particularly the embodiments as discussed herein, utilizing a machine learning model, determines one or more predicted splinting points in the inspiration of a patient and applies electrical pulses during the predicted splinting points so as to assist the patient breathe to a complete and full breath.

Definitions

The term "breathing cycle" reflects an inspiration and expiration cycle of a monitored individual. A breathing cycle may include patches, hitches, abrupt stops, and/or other interruptions in the inspiration portion of the breathing cycle. These interruptions may be indicative of splinting. As used herein, a breathing cycle without interruption in the inspiration is considered a normal breath (alternatively referred to as a "full" breath).

The term "splinting" may refer to shortening of breath during a breathing cycle. The patient may, for example, consciously or subconsciously shorten the inspiration portion of the patient's breath to avoid painful portions of a full (normal) breath cycle. An occurrence of splinting in a breathing cycle of a patient may be identified by a trained machine learning model by processing captured breathing pattern sensory data of the patient. In some embodiments, splinting may be determined by processing (e.g., using a trained machine learning model) the breathing pattern sensory data as determined based at least in part on comparing one or more breathing waveform data to one or more expected breathing waveform data. A breathing cycle where inspiration is completed but is interrupted (e.g., due to pain) is considered partial splinting and a breathing cycle where the inspiration is abruptly stopped (e.g., due to pain) without completing inspiration is considered full splinting.

The term "breathing pattern sensory data" refers to a data object (or collection of data objects) that describes breathing measurements reflected within data collected from a sensor device (e.g., breathing monitoring device) that monitors a patient's breathing. The sensor device generates variable, detectable voltage signals resulting from changes in electrical resistance measured across the device. These voltage signals can be correlated to a breathing pattern of the patient. The sensor device includes one or more sensors. The one or more sensors may include sensors that are in direct contact with the patient's body and/or sensors that are not in direct contact with the patient's body. For example, the one or more sensors may be integrated and/or secured to a wearable device (e.g., band-aid, a vest, shirt, body band, and/or the like). In example embodiments, the one or more sensors include a stretch sensor integrated and/or secured to a stretchable wearable device configured to be positioned adjacent the chest (or diaphragm) of the patient. The sensor device is configured to capture the breathing measurements and to transmit (e.g., wirelessly, through a wired transmission medium, and/or the like) the captured breathing measurements to a computing device configured to store the breathing measurements and/or generate breathing waveform data based at least in part on the breathing measurements.

The term "machine learning model" comprises parameters, hyper-parameters, defined operations, and/or defined mappings of a model that is configured to process one or more prediction input values (e.g., one or more selected breathing measurements) in accordance with one or more trained parameters of the machine learning models in order to generate a prediction. Machine learning models of certain embodiments are executable based at least in part on received input data (e.g., data reflecting a patient's breathing pattern) and may generate data outputs as discussed herein. Aspects of example of a machine learning model may implement a mathematically derived algorithm (MDA). An MDA may comprise any algorithm trained using training data to predict one or more outcome variables. Without limitation, a model may comprise and/or otherwise implement machine learning frameworks including neural networks, support vector machines, gradient boosts, Markov models, adaptive Bayesian techniques, and statistical models (e.g., timeseries-based forecast models such as autoregressive models, autoregressive moving average models, and/or an autoregressive integrating moving average models). Additionally and without limitation, a machine learning model, as used in the singular, may include ensembles using multiple machine learning and/or statistical techniques.

The term "breathing waveform data" refers to a graphical representation (e.g., periodic wave pattern) of a current (e.g., real time) breathing cycle of a patient that is generated by processing captured breathing pattern sensory data of the patient, and defined by an upward trajectory (during inhalation) and ending at a peak defining full lung capacity, and a downward trajectory (during exhalation) defining a minimum/trough for empty lung capacity. The graphical depiction may be substantially triangular, substantially hyperbolic, and/or the like. As an example, in an example embodiment, the breathing waveform data may define a substantially triangular pattern on graphical depiction of the patient's breathing, where the left portion (e.g., the left half) of the substantially triangular waveform data describes the inspiration pattern for the patient with respect to the captured breathing pattern sensory data and the right portion (e.g., the right half) of the substantially triangular breathing waveform data describes the expiration pattern for the patient with respect to the captured breathing pattern sensory data. Breathing waveform data may be characterized by one or more attributes (e.g., a peak inspiration, a time from the beginning of inspiration reflected within the breathing waveform data to the peak inspiration reflected within the breathing waveform data, a time from the peak inspiration reflected within the breathing waveform data to the end of expiration reflected within the breathing waveform data, and/or the like).

The term "expected breathing waveform data" refers to a graphical representation of an expected breathing cycle of patient defined by an upward trajectory (during inhalation) and ending at a peak defining full lung capacity, and a downward trajectory (during exhalation) defining a minimum/trough for empty lung capacity. The graphical depiction may be substantially triangular, substantially hyperbolic, and/or the like. In certain embodiments, expected breathing waveform data may be generated by processing breathing pattern sensory data collected during a known breathing cycle of the patient that is not characterized by splinting occurring during the breathing cycle. The breathing measurements of the patient may be measured when the patient inspires and expires without an interruption in the inspiration portion of the breathing cycle that is indicative of splinting. In an example embodiment, the breathing measurements may be measured under the supervision of a physician, a nurse, and/or the like. In some embodiments, the breathing measurements may be measured over a period of time. In an example embodiment, the breathing waveform data may define a substantially triangular pattern on graphical depiction of the patient's breathing, where the left portion (e.g., the left half) of the substantially triangular pattern describes the inspiration of the patient and the right portion (e.g., the right half) of the substantially triangular pattern describes the expiration of the patient. Expected breathing waveform data may comprise one or more attributes (e.g., expected peak inspiration, a time from the beginning of inspiration reflected within the expected breathing waveform data to the expected peak inspiration reflected within the breathing waveform data, a time from the expected peak inspiration reflected within the expected breathing waveform data to the end of expiration reflected within the expected breathing waveform data, and/or the like).

The term "predicted interruption score" refers to a data object that describes a value that in turn describes the likelihood that splinting is reflected within breathing waveform data reflecting a breathing cycle of inspiration and expiration of a patient. A predicted interruption score of certain embodiments is generated by a trained machine learning model by processing breathing waveform data for a corresponding patient. For example, the predicted interruption score for a patient may be generated by comparing breathing waveform data of the monitored individual with one or more expected breathing waveform data utilizing a trained machine learning model. The predicted interruption score may be a Boolean value (e.g., where a one-valued predicted interruption score may represent that splinting is reflected within a corresponding breathing waveform data, while a zero-valued predicted interruption score may represent that splinting is not reflected within corresponding breathing waveform data). In example embodiments, the predicted interruption score may be a non-Boolean value. In various embodiments, the predicted interruption score may be a vector.

The term "stimulation signal" refers to a stimulation (e.g., electrical stimulation) such as transcutaneous electrical nerve stimulation (TENS) provided (e.g., delivered, applied, or the like) to a patient's body (e.g., target nerves) in order to assist the patient breathe through a splinting point. Characteristics of stimulation signals may be defined by one or more parameters including, without limitation, intensity (e.g., defined by amplitude, voltage, and/or current characteristics), duration (e.g., pulse duration), wave form (e.g., triangular, rectangular, and/or the like). In some embodiments, a stimulation signal may target one or more regions (e.g., nerves, muscles, and/or the like) of the patient's body.

The term "stimulation schedule" defines one or more stimulation triggers configured to trigger (e.g., prompt) a stimulator apparatus to transmit a stimulation signal to a patient. Each stimulation trigger of the one or more stimulation triggers is associated with an emit timestamp (that represents the timing to trigger the stimulator apparatus) and correlates with a detected splinting point reflected within breathing waveform data reflecting a breathing cycle of the patient. In some embodiments, a stimulation schedule may be stored by one or more computing entities.

Computer Program Products, Methods, and Computing Devices

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all non-transitory computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like). A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

Exemplary System Architecture

FIG. 1 provides an example system architecture 100 that can be used in conjunction with various embodiments of the present invention. As shown in FIG. 1, the system architecture 100 may comprise one or more management computing entities 10, one or more user computing entities 20, one or more networks 30, one or more breathing monitoring device 40, one or more stimulator apparatus 60 and/or the like. Each of the components of the system may be in electronic communication with, for example, one another over the same or different wireless or wired networks 30 including, for example, a wired or wireless Personal Area Network (PAN), Local Area Network (LAN), Metropolitan Area Network (MAN), Wide Area Network (WAN), and/or the like. Additionally, while FIG. 1 illustrates certain system devices as separate, standalone devices, the various embodiments are not limited to this particular architecture.

Exemplary Management Computing Entity

Figure 2:
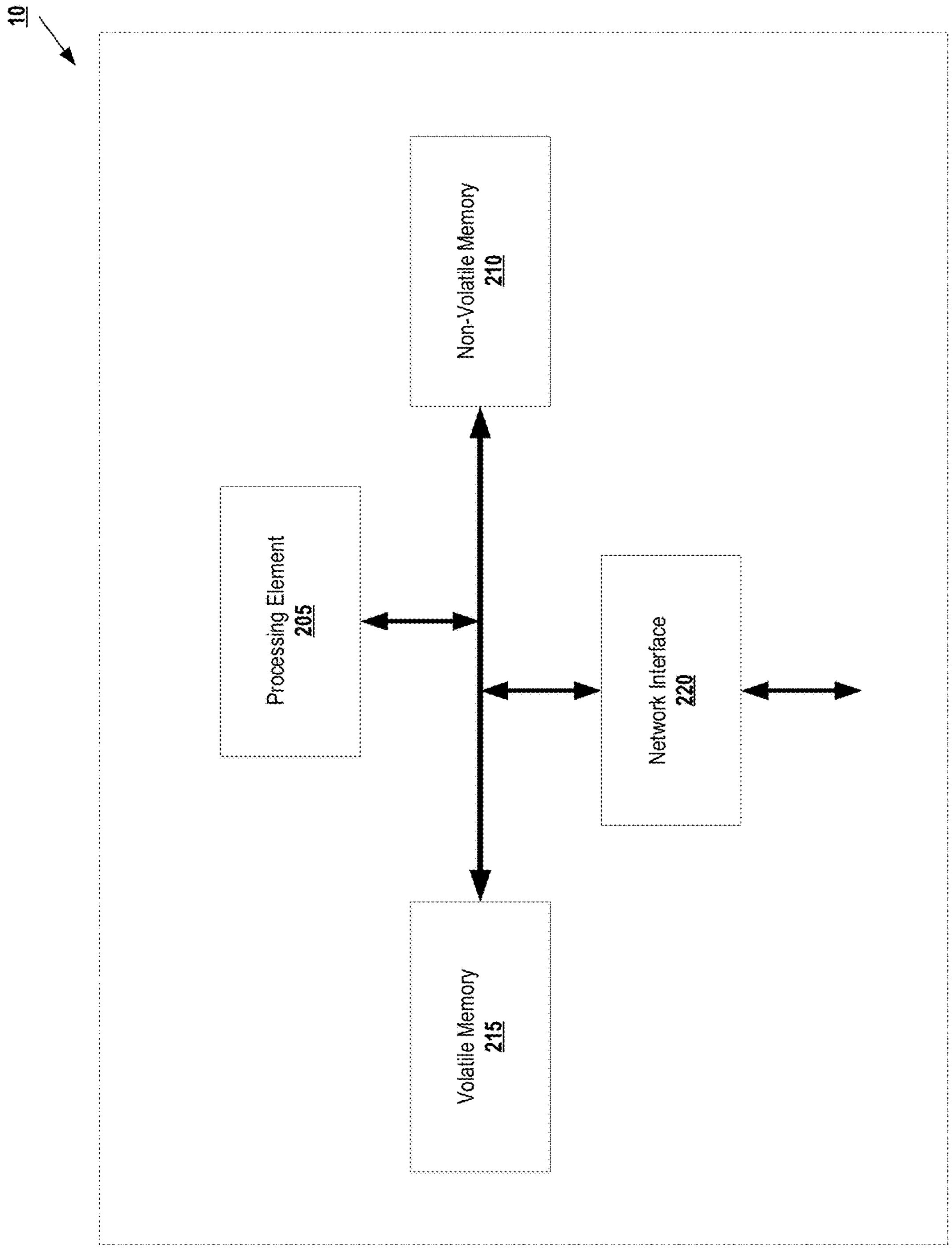
FIG. 2 is an example schematic of a management computing entity in accordance with certain embodiments.

FIG. 2 provides a schematic of a management computing entity 10 according to one embodiment of the present invention. In general, the terms computing device, entity, device, system, and/or similar words used herein interchangeably may refer to, for example, one or more computers, computing devices, computing entities, desktop computers, mobile phones, tablets, phablets, notebooks, laptops, distributed systems, terminals, servers or server networks, blades, gateways, switches, processing devices, set-top boxes, relays, routers, network access points, base stations, the like, and/or any combination of devices adapted to perform the functions, operations, and/or processes described herein. Such functions, operations, and/or processes may include, for example, transmitting, receiving, operating on, processing, displaying, storing, determining, generating/creating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the management computing entity 10 may also include one or more network and/or communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the management computing entity 10 may include or be in communication with one or more processing elements 205 (also referred to as processors, processing circuitry, and/or similar terms used herein interchangeably) that communicate with other elements within the management computing entity 10 via a bus, for example. As will be understood, the processing element 205 may be embodied in a number of different ways. For example, the processing element 205 may be embodied as one or more complex programmable logic devices (CPLDs), microprocessors, multi-core processors, coprocessing devices, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the management computing entity 10 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like.

As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably may refer to a structured collection of records or information/data that is stored in a computer-readable storage medium, such as via a relational database, hierarchical database, and/or network database.

In one embodiment, the management computing entity 10 may further include or be in communication with volatile media (also referred to as volatile storage, memory, memory storage, memory circuitry and/or similar terms used herein interchangeably). In one embodiment, the volatile storage or memory may also include one or more volatile storage or memory media 215 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the management computing entity 10 with the assistance of the processing element 205 and the operating system.

As indicated, in one embodiment, the management computing entity 10 may also include one or more network and/or communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, management computing entity 10 may be configured to communicate via wireless external communication networks using any of a variety of protocols, such as general packet radio service (GPRS), Universal Mobile Telecommunications System (UMTS), Code Division Multiple Access 200 (CDMA200), CDMA200 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), IR protocols, NFC protocols, RFID protocols, IR protocols, ZigBee protocols, Z-Wave protocols, 6LoWPAN protocols, Wibree, Bluetooth protocols, wireless universal serial bus (USB) protocols, and/or any other wireless protocol. The management computing entity 10 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the management computing entity's components may be located remotely from other management computing entity 10 components, such as in a distributed system. Furthermore, one or more of the components may be aggregated and additional components performing functions described herein may be included in the management computing entity 10. Thus, the management computing entity 10 can be adapted to accommodate a variety of needs and circumstances, such as including various components described with regard to a mobile application executing on the user computing entity 20, including various input/output interfaces.

Exemplary User Computing Entity

Figure 3:
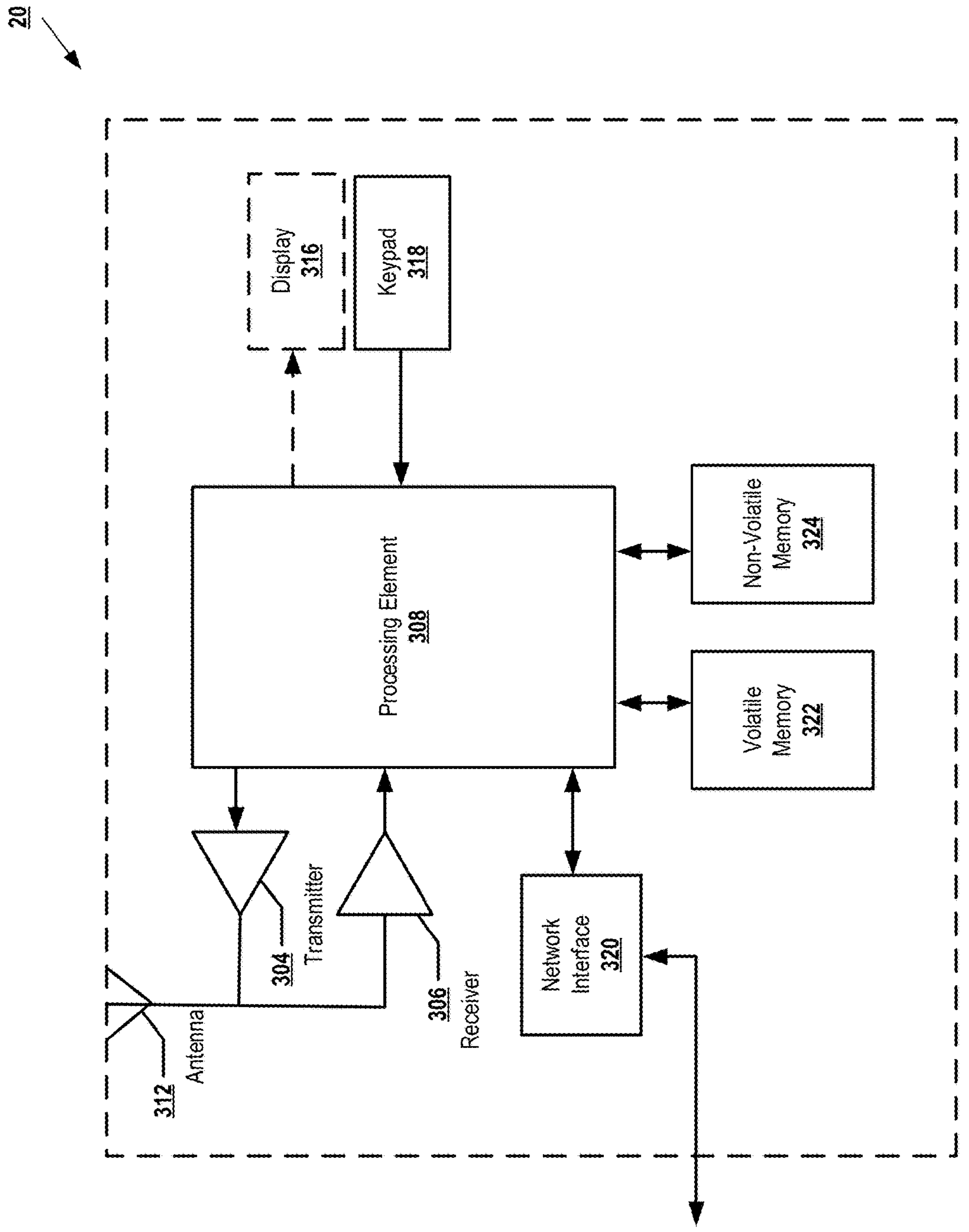
FIG. 3 is an example schematic of a user computing entity in accordance with certain embodiments.

FIG. 3 provides an illustrative schematic representative of user computing entity 20 that can be used in conjunction with embodiments of the present invention. In various embodiments, the user computing entity 20 may be or comprise one or more mobile devices, wearable computing devices, and/or the like.

As shown in FIG. 3, a user computing entity 20 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various devices, such as a management computing entity 10, another user computing entity 20, and/or the like. In an example embodiment, the transmitter 304 and/or receiver 306 are configured to communicate via one or more SRC protocols. For example, the transmitter 304 and/or receiver 306 may be configured to transmit and/or receive information/data, transmissions, and/or the like of at least one of Bluetooth protocols, low energy Bluetooth protocols, NFC protocols, RFID protocols, IR protocols, Wi-Fi protocols, ZigBee protocols, Z-Wave protocols, 6LoWPAN protocols, and/or other short range communication protocol. In various embodiments, the antenna 312, transmitter 304, and receiver 306 may be configured to communicate via one or more long range protocols, such as GPRS, UMTS, CDMA200, 1×RTT, WCDMA, GSM, EDGE, TD-SCDMA, LTE, E-UTRAN, EVDO, HSPA, HSDPA, Wi-Fi, Wi-Fi Direct, WiMAX, and/or the like. The user computing entity 20 may also include one or more network and/or communications interfaces 320 for communicating with various computing entities, such as by communicating data, content, information, and/or similar terms used herein interchangeably that can be transmitted, received, operated on, processed, displayed, stored, and/or the like.

In this regard, the user computing entity 20 may be capable of operating with one or more air interface standards, communication protocols, modulation types, and access types. More particularly, the user computing entity 20 may operate in accordance with any of a number of wireless communication standards and protocols. In a particular embodiment, the user computing entity 20 may operate in accordance with multiple wireless communication standards and protocols, such as GPRS, UMTS, CDMA200, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 20 can communicate with various other devices using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 20 can also download changes, add-ons, and updates, for instance, to its firmware, software (e.g., including executable instructions, applications, program modules), and operating system.

According to one embodiment, the user computing entity 20 may include location determining aspects, devices, modules, functionalities, and/or similar words used herein interchangeably to acquire location information/data regularly, continuously, or in response to certain triggers. For example, the user computing entity 20 may include outdoor positioning aspects, such as a location module adapted to acquire, for example, latitude, longitude, altitude, geocode, course, direction, heading, speed, UTC, date, and/or various other information/data. In one embodiment, the location module can acquire information/data, sometimes known as ephemeris information/data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the apparatus's 30 position in connection with a variety of other systems, including cellular towers, Wi-Fi access points, and/or the like. Similarly, the user computing entity 20 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing entities (e.g., smartphones, laptops) and/or the like. For instance, such technologies may include iBeacons, Gimbal proximity beacons, BLE transmitters, NFC transmitters, and/or the like. These indoor positioning aspects can be used in a variety of settings to determine the location of someone or something to within inches or centimeters.

The user computing entity 20 may also comprise a user interface device comprising one or more user input/output interfaces (e.g., a display 316 and/or speaker/speaker driver coupled to a processing element 308 and a touch interface, keyboard, mouse, and/or microphone coupled to a processing element 308). For example, the user interface may be configured to provide a mobile application, browser, interactive user interface, dashboard, webpage, and/or similar words used herein interchangeably executing on and/or accessible via the user computing entity 20 to cause display or audible presentation of information/data and for user interaction therewith via one or more user input interfaces. Moreover, the user interface can comprise or be in communication with any of a number of devices allowing the user computing entity 20 to receive information/data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 20 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 20 can capture, collect, store information/data, user interaction/input, and/or the like.

The user computing entity 20 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, information/data, applications, programs, program modules, scripts, source code, object code, byte code, compiled code, interpreted code, machine code, executable instructions, and/or the like to implement the functions of the user computing entity 20.

Exemplary Networks

In one embodiment, any two or more of the illustrative components of the system architecture 100 of FIG. 1 may be configured to communicate with one another via one or more networks 30. The networks 30 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 30 may have any suitable communication range associated therewith and may include, for example, global networks (e.g., the Internet), MANs, WANs, LANs, or PANs. In addition, the networks 30 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

Exemplary Breathing Monitoring Device

Figure 4:
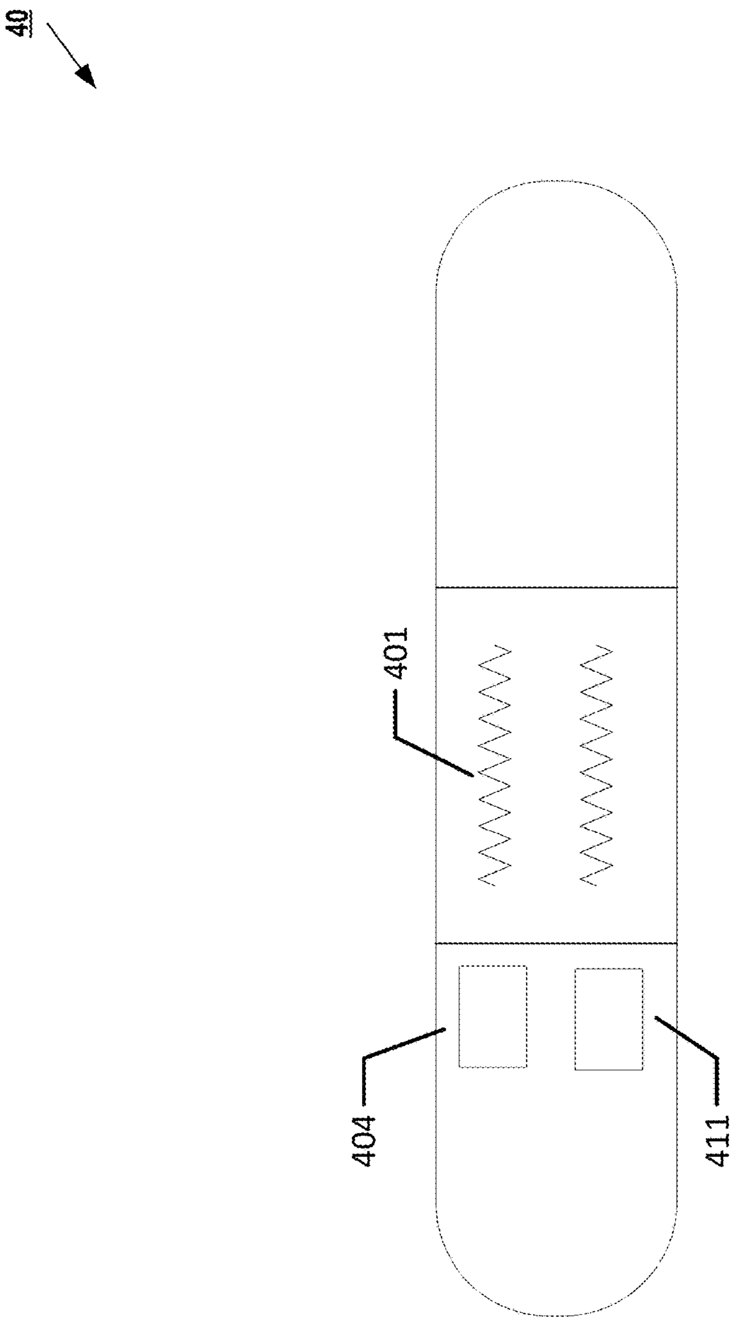
FIG. 4 is an example schematic of a breathing monitoring device in accordance with certain embodiments.

FIG. 4 illustrates an example breathing monitoring device 40 (alternatively referred to as breathing sensor). In some embodiments, the breathing monitoring device 40 may be embodied as a non-wearable device. In some embodiments, the breathing monitoring device may be embodied as a wearable device having one or more sensors incorporated therein. The one or more sensors may include strain gauges, stretch sensors, and/or other sensor types configured to have detectable changes in characteristics (e.g., electrical resistance) that may be detected (e.g., at a remote computing device), in response to physical changes of the one or more sensors (e.g., changes to a sensor caused by the rising and falling of the patient's chest and/or contraction and expansion of the diaphragm).

In the noted wearable device, the one or more sensors may be arranged over a particular area of the wearable device (e.g., an area expected to cover one or more target organs, target muscles, and/or the like) when worn by a patient. In the embodiments discussed in detail herein, as illustrated in FIG. 4, the breathing monitoring device 40 is embodied as an adhesive style (e.g., patch style) wearable device configured to be adhered to the skin of the patient over an area of the patient's body that moves upon the patient breathing (e.g., proximate the patient's lungs). However, the breathing monitoring device 40 may alternatively be embodied, for example and without limitation, as a vest, jacket, shirt, band, belt and/or the like including at least one sensor positioned to detect movement of the patient's chest and/or diaphragm, for example, as the patient breathes.

The breathing monitoring device 40 is configured to monitor a user's (e.g., patient) breathing and receive and/or transmit data/information from the breathing monitoring device 40. As depicted in FIG. 4, the example breathing monitoring device 40 comprises a controller 404 (e.g., a processing circuitry, computing device, one or more computer processors) having a wireless communication transceiver, Bluetooth Low Energy (BLE), and/or the like. The controller 404 is integrated into the breathing monitoring device 40 and may be in wired or wireless communication with one or more sensors of the breathing monitoring device 40, the power supply 411 of the breathing monitoring device 40, the management computing entity 10, and/or the user computing entity 20. Accordingly, the breathing monitoring device 40 comprises a communications interface configured to enable the breathing monitoring device to communicate with the management computing entity 10 and/or user computing entity 20 in a wired and/or wireless manner (e.g., via network 30). However, the controller 404 of the breathing monitoring device 40 may be in wireless communication with, but physically distinct from the breathing monitoring device 40 (e.g., via short-range wireless communication, such as Bluetooth, via long-range wireless communication, and/or the like).

The controller 404 of the breathing monitoring device 40 may be configured to (e.g., alone or together with the management computing entity 10) provide appropriate signals to elements of the breathing monitoring device 40. In some embodiments, the controller 404 may comprise a user interface device (not shown) comprising one or more user input/output interfaces (e.g., a button and/or speaker/speaker driver coupled to a processing element and/or controller/processor and a touch interface, and/or microphone coupled to a processing element and/or controller). For example, the user interface may be configured to cause display or audible presentation of information/data and for user interaction therewith via one or more user input interfaces. The controller 404 may store instructions/parameters required for various operations by the breathing monitoring device 40. In various embodiments, the controller 404 of the breathing monitoring device 40 may comprise components similar to the user computing entity 20 depicted in FIG. 3.

As noted, FIG. 4 illustrates an example breathing monitoring device 40 embodied as an adhesive style wearable device that may be adhered to the patient's skin. The example breathing monitoring device 40 comprises an article/material extending along a length and having an inner portion configured to be adhered to the skin of the wearer. Accordingly, the inner portion of the breathing monitoring device 40 comprise an adhesive material and/or the like configured to releasably secure the breathing monitoring device 40 to the skin of a patient. The article/material may be a flexible material (e.g., elastic material) such that the breathing monitoring device 40 may be placed under tension when worn, such that additional included elements (e.g., sensors, batteries, and/or the like) may remain tightly placed against the patient's body during normal movement of the user (e.g., sitting, standing, running, and/or the like). For example, a flexible material may comprise a flexible fabric, a flexible non-woven material, a flexible polymeric material, and/or the like. A flexible material may have stretchable properties. However, the article/material of the wearable breathing monitoring device 40 may be inflexible.

As shown in FIG. 4, the example breathing monitoring device 40 comprises one or more sensors 401 as discussed above. The one or more sensors 401 may be positioned at least partially on an interior surface of the wearable portion of the breathing monitoring device 40. The one or more sensors are configured to monitor a patient's breathing and to generate data indicative of the patient's current breathing. For example, the one or more sensors are configured to capture raw sensor data (e.g., voltage signals) and provide the raw sensor data or pre-processed sensor data to the controller 404. As noted, the one or more sensors 401 of the breathing monitoring device 40 may be in electronic communication with the controller 404 of the breathing monitoring device such that it can exchange information/data (e.g., receive and transmit data) with the breathing monitoring device 40. In some embodiments, the one or more sensors 401 are configured for receiving and/or capturing information/data regularly, continuously, and/or in response to certain triggers.

In some embodiments, received raw sensor data from the one or more sensors may be analyzed and/or processed locally by the controller 404 of the breathing monitoring device 40, processed locally by the controller 404 with remote assistance from the management computing entity 10 and/or user computing entity 20 (e.g., by passing at least a portion of the received sensor data to the management computing entity 10 and/or user computing entity 20 for remote processing), or processed via the management computing entity 10 and/or user computing entity 20. In some embodiments, as part of processing, the controller 404 of the breathing monitoring device may be configured to locally execute various algorithms on at least a portion of the raw and/or processed information/data obtained by the breathing monitoring device 40. In other embodiments, the controller 404 of the breathing monitoring device 40 transmits (periodically or on request) data object describing at least a portion of the raw and/or processed information/data for processing by the management computing entity 10/and or user computing entity 20. In some embodiments, (e.g., as part of processing the raw data received from the one or more sensor), the controller 404 of the breathing monitoring device 40 may be configured to receive data objects describing additional information (e.g., physiological data, biometric data) from a user computing entity 20 and/or from the management computing entity 10. In some embodiments, processing the sensor data may comprise providing at least a portion of the sensor data (e.g., pre-processed data) as input to a machine-learning model. The controller 404 of the breathing monitoring device 40 may cause the one or more sensors of the breathing monitoring device 40 to begin monitoring/measuring the breathing of the user/patient.

As depicted in FIG. 4, the example wearable breathing monitoring device 40 comprises one or more stretch sensors. Particularly, in the embodiment of FIG. 4, the breathing monitoring device 40 comprises a fabric-based stretch sensor configured for measuring changes in resistance of the stretch sensing fabric (or conductive contacts embedded within the stretch-sensing fabric) as it stretches and relaxes in response to contraction and expansion of the user's diaphragm (or rise and fall of the user's chest) as the user inspires and expires, thereby generating breathing pattern sensory data.

As shown in FIG. 4, the example breathing monitoring device 40 comprises a power source 411 (e.g., one or more batteries) to provide power to the onboard controller 404, to provide power to the one or more sensors 401, and/or other elements of the breathing monitoring device 40. As illustrated in FIG. 4, the power source 411 may be a self-charging battery (e.g., a body-heat self-charging battery). In various embodiments, the breathing monitoring device 40 may further comprise volatile and/or non-volatile memory. In various embodiments, the breathing monitoring device may further comprise input/output circuitry.

Exemplary Stimulator Apparatus

Figures 5A, 5B:
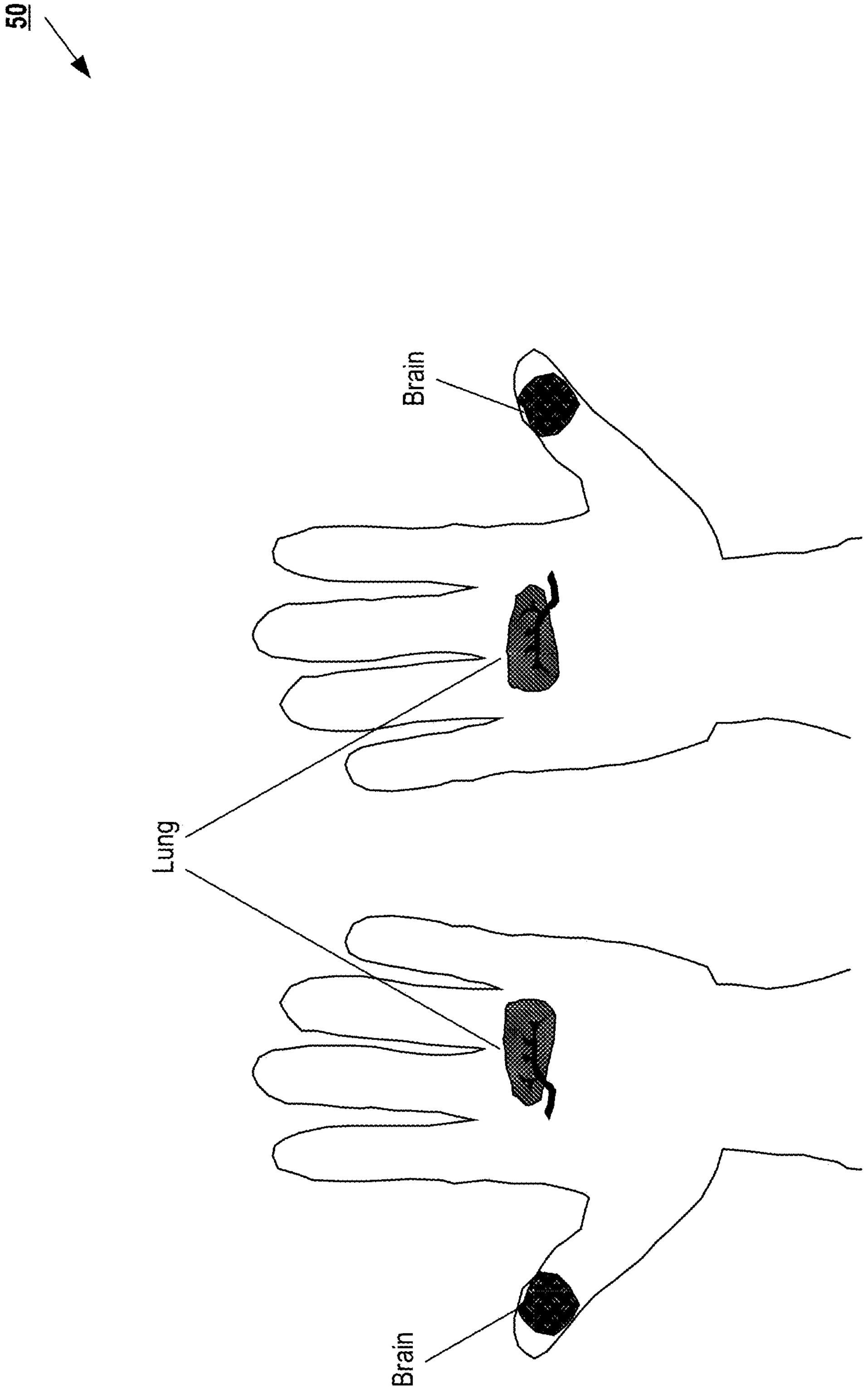
FIGS. 5A-5B are illustrations of nerve systems within a human body that may be stimulated in accordance with certain embodiments.
Figure 6:
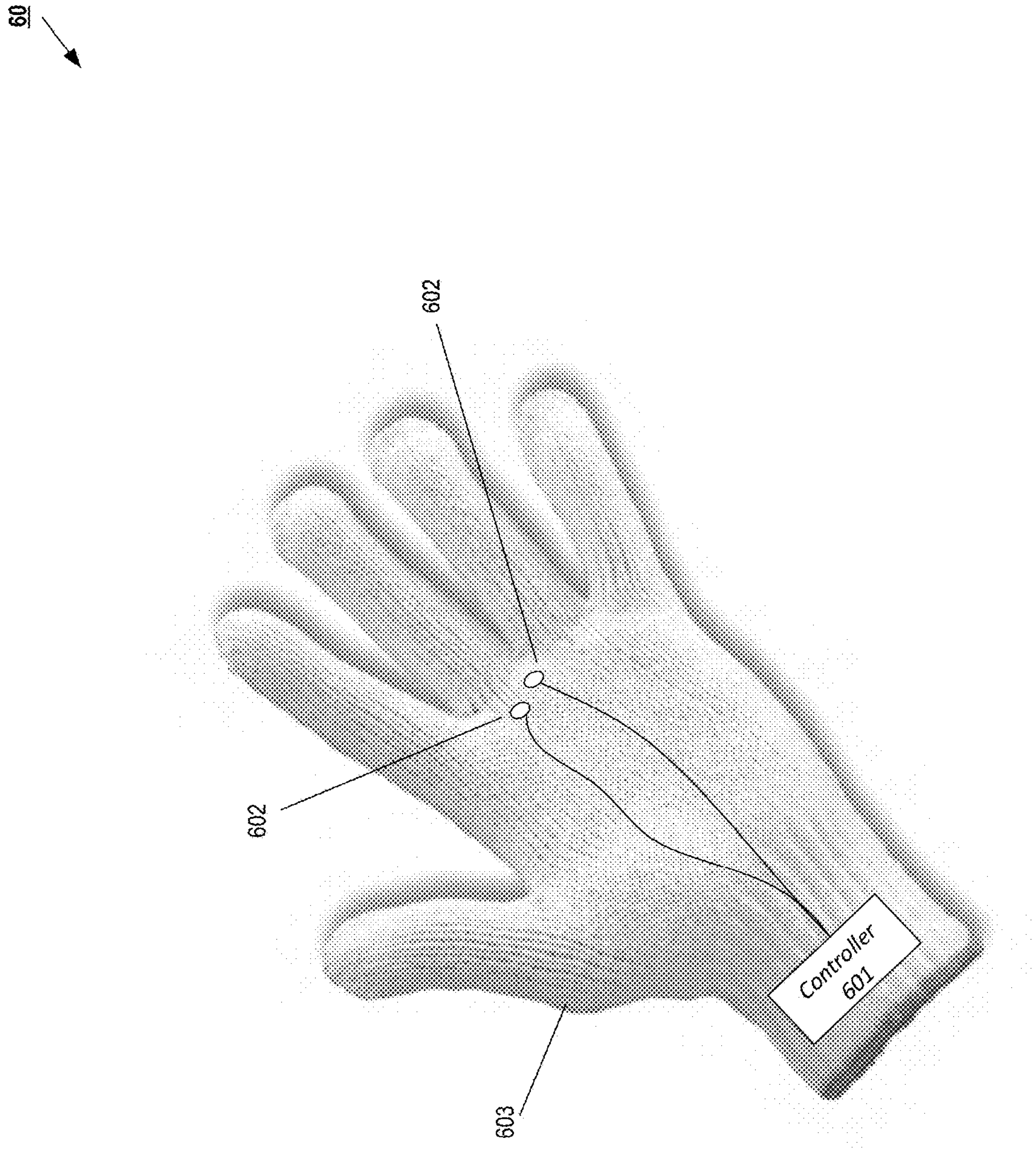
FIG. 6 is an example stimulator apparatus according to certain embodiments.

FIG. 6 illustrates an example stimulator apparatus 60, with FIGS. 5A-5B providing an illustration of nerve system within a human hand that correlates with the example stimulator apparatus 60 of FIG. 6. Specifically, FIG. 6 is a wearable stimulator apparatus 60 (a glove) configured to provide stimulation signals to the patient's hand. However, the stimulator apparatus 60 may be a non-wearable stimulator apparatus.

As shown in the example embodiment of FIG. 6, a stimulator apparatus 60 comprises a controller 601 in electronic communication with one or more transmitters 602 configured for emitting stimulation signals. As shown in FIG. 6, the one or more transmitters 602 is positioned within a body 603 of the stimulator apparatus 60. For example, the one or more transmitters 602 is configured for emitting a signal that may be felt by a human user of the stimulator apparatus 60. As examples, the one or more transmitters 602 may be electrical contacts that are configured to generate a low-voltage shock that may be felt by a patient; vibrators that are configured to generate high-frequency vibrations that may be felt by a patient; resistance heaters that are configured to quickly heat to a high temperature that may be detected by a patient; actuators that are configured to move a plunger, a needle, or another object into the surface of the patient's skin such that the patient can detect the increase in pressure provided by the actuated object; and/or the like. As a specific example, the one or more transmitters 602 may be transcutaneous electrical nerve stimulation (TENS) devices. In some embodiments, a stimulation signal is embodied as one of an electrical pulse, a vibration, or a heat signal.

In the illustrated example embodiments of FIG. 6, the one or more transmitters 602 are in wired communication with the controller 601, thereby enabling the controller 601 to provide power signals to the one or more transmitters 602 to operate the one or more transmitters 602 during operation as discussed below. However, the one or more transmitters 602 may be in wireless communication with the controller 601. The controller 601 may be configured to operate the one or more transmitters 602 simultaneously, such as operating a single transmitter 602 (to emit a stimulation signal from a single transmitter 602 to the patient), or operating a plurality of transmitters 602 simultaneously (to emit a stimulation signal from the plurality of transmitters 602 simultaneously to the patient).

The transmitters 602 may be low-profile transmitters that, when not in operation for emitting signals, may be undetectable or at least substantially undetectable by the patient. For example, for transmitters located on an inner-part of the patient's hand when worn in a glove-like wearable stimulator apparatus 60, the one or more transmitters 602 are sufficiently thin that the patient cannot easily distinguish between the thickness of the glove and the thickness of the one or more transmitters 602.

Moreover, wearable stimulator apparatus 60 may have a body 603 configured to contour to a specific portion of a human body (or to the shape of another living patient). As shown, the stimulator apparatus 60 is configured to contour to a human hand. The body 603 may comprise a flexible or semi-rigid material. In certain embodiments, portions of the body 603 may comprise a flexible material and other portions of the body 603 may comprise a semi-rigid material. For example, a flexible material may comprise a flexible fabric, a flexible non-woven material, a flexible polymeric material, and/or the like. A flexible material may have stretchable properties. A semi-rigid material may comprise a foam material, a polymeric material that resists bending, and/or the like. Although not shown in the figures, the body 603 may comprise one or more rigid components, such as braces, hinges, and/or the like, to further ensure proper positioning of the wearable stimulator apparatus 60. The wearable stimulator apparatus 60 may be custom formed for a particular patient, or the wearable stimulator apparatus 60 may be provided to fit a plurality of patients. The wearable stimulator apparatus 60 may be provided in a plurality of discrete sizes (e.g., small, medium, large, extra-large) to accommodate a plurality of patients having similar sized features.

The controller 601 of the example embodiments has certain components and/or functionality analogous to a user computing entity 20. In certain embodiments, the controller 601 additionally includes an onboard power-supply, such as a rechargeable battery, a replaceable battery, and/or the like. The controller 601 is configured for wireless communication with other computing entities, such as via short-range wireless communication protocols (e.g., Bluetooth) or longer-range wireless communication protocols (e.g., Wi-Fi). The controller 601 is thus network connectable, such that the controller 601 can connect with the Internet. In certain embodiments, the stimulator apparatus 60 (inclusive of the controller 601) may be embodied as an Internet of Things (IoT) device configured for exchanging data with a remotely located management computing entity 10 via the Internet. In other embodiments, such as those embodiments in which the controller 601 is configured to wirelessly communicate with other computing entities via short-range wireless communication protocols, the stimulator apparatus 60 may communicate indirectly with a management computing entity 10, such as by providing data to a user computing entity 20 in wireless communication with the stimulator apparatus 60, and causing the user computing entity 20 to transmit the data to the management computing entity 10.

In certain embodiments, the controller 601 may be detachably secured onto/within the stimulator apparatus 60. Particularly for wearable stimulator apparatuses such as the embodiment of FIG. 6, the controller 601 may be removed to facilitate washing of the body 603. In such embodiments, the individual transmitters 602 may be removable from the body 603, or the individual transmitters 602 may be washable, such that the individual transmitters 602 are not damaged if they remain within the body 603 during washing (e.g., water-based and/or soap-based washing). As an example, the controller 601 may include a connector for connecting with a mated connector at an end of one or more wires connected to the one or more transmitters 602. The connector can be disconnected to enable the controller 601 to be removed from the body 603 of the stimulator apparatus 60.

With reference to the stimulator apparatus 60 of FIG. 6 and the schematic drawings of nerve placement within a human hand of FIGS. 5A-5B, the one or more transmitters 602 are positioned within the body 603 of the stimulator apparatus 60 to stimulate individual nerves (or specific families of nerve endings) of the patient. The locations of the one or more transmitters 602 within a stimulator apparatus 60 may be established and/or optimized through any of a variety of processes, such as through machine-learning based models for selecting effective locations for placement of the one or more transmitters 602 within a stimulator apparatus 60. In certain embodiments, the stimulator apparatus 60 has transmitters located at a plurality of regions within the stimulator apparatus 60, and the selection of a particular transmitter (or group of transmitters) to be used for stimulation of the patient may be selected via any of a variety of processes (e.g., machine-learning, based at least in part on training data collected for the specific patient or a plurality of patients). As shown in the schematic of FIGS. 5A-5B, a human hand has a plurality of discrete regions that are believed to correlate (e.g., have a sensory impact on) to different organs of the human body. It is believed that stimulation of the discrete regions (e.g., discrete groupings of nerve endings) within the human hand relieves or otherwise lessens pain felt in the corresponding organ (e.g., lung). The inventors hypothesize that nerve stimulation—particularly when the nerve stimulation is directed to those nerves (or groups of nerve endings) that are determined to correspond to the lungs—may cause the patient's body to generate nervous system signals within the patient's body that serve to lessen the patient's perceived pain or discomfort that arises from the patient's lungs during breathing. As shown in FIGS. 5A-5B, it is believed that the upper palm region of the human hand corresponds to the human lung. The one or more transmitters 602 may be positioned within the stimulator apparatus so as to stimulate a single region (e.g., upper palm) of the patient's hand when the stimulator apparatus 60 is worn by the patient, thus targeting the corresponding organ. In example embodiments, the one or more transmitters 602 may be positioned within the stimulator apparatus 60 so as to stimulate different regions of the patient's hand, thus targeting different corresponding organs.

The example of FIG. 6 is provided as a non-limiting example, and it should be understood that other configurations, such as to accommodate other parts of human body, may be provided in certain embodiments. For example, a wearable or non-wearable stimulator apparatus may be provided for applying stimulator signal to a patient's foot, patient's leg, patient's torso, patient's arm, and/or the like. For example, in some embodiments, the stimulator apparatus 60 may be embodied in a wearable sock (not shown) configured to provide stimulation signals to the patient's foot/leg.

Example System Operation

The operation of various embodiments of the present invention will now be described. As discussed herein, various embodiments are directed to systems and methods for the automated detection and/or identification of splinting points (e.g., pain points) in captured breathing pattern sensory data corresponding to a breathing cycle (lung inspiration and expiration) of a monitored individual (e.g., patient). Although the following exemplary operations are described as being performed by one of the breathing monitoring device 40, the management computing entity 10, the user computing entity 20, and/or the stimulator apparatus 60, in various embodiments the operations can be interchangeably performed by other components within the system architecture 100.

In various embodiments, a breathing monitoring device 40 comprising one or more sensors 401 is positioned with respect to the monitored individual's body so as to monitor the patient's breathing. As noted above, the breathing monitoring device 40 may comprise a wearable portion, such as an adhesive-based device that may be adhered to the patient's skin, having the one or more sensors 401 integrated therein and/or secured thereto. In other embodiments, the breathing monitoring device 40 may be positioned such that an effective field of view of the device (the area to be monitored by the device) encompasses the patient's chest. For example, the wearable portion may comprise one or more stretch sensors configured for capturing signals that may be used to obtain and/or calculate breathing pattern sensory data, which is in turn may be used to generate breathing waveform data reflecting a breathing cycle of inspiration and expiration of the monitored individual. For example, the breathing monitoring device 40 may comprise a stretch sensor (comprising a stretch sensing fabric, strain gauge, electrical conductor, and/or the like) configured for measuring a stretch of the wearable portion of the breathing monitoring device 40 as the monitored individual's diaphragm contracts and expands during inspiration and expiration. As another example, the breathing monitoring device 40 may comprise a visual-based monitoring device (e.g., using a camera or other imaging device) to detect movements of the patient's chest to monitor the patient's breathing. In some embodiments, Eulerian Video Magnification may be utilized to monitor the breathing pattern of a monitored individual and to detect interruptions, slow progression in inspiration (e.g., slow progression after fast or choppy inspiration), and/or the like in the inspiration of the monitored individual reflected in the breathing pattern.

In various embodiments, the breathing monitoring device 40 may be in communication with a user computing entity 20, a management computing entity 10, a stimulator apparatus 60, and/or a network 30. In various embodiments, the management computing entity 10 may cause operation of a breathing monitoring device 40. For example, the management computing entity 10 may be configured and/or programmed to control one or more functions of a breathing monitoring device 40 in communication with the management computing entity 10.

In some embodiments, the breathing monitoring device 40 may be in wired or wireless communication with a user computing entity 20 (e.g., co-located, for example within the same room as the breathing monitoring device 40). In the noted embodiments, a user computing entity 20 may operate a monitoring application (e.g., stored in memory 322, 324 and executed by processing element 308) that may be configured and/or programmed to control one or more functions of a breathing monitoring device 40 in communication with the user computing entity 20.

In an example embodiment, a user computing entity 20 and/or a management computing entity 10 may receive and/or obtain breathing pattern sensory data (and possible corresponding metadata) and perform analysis and processing of the breathing pattern sensory data. For example, the breathing monitoring device 40 may capture breathing pattern sensory data and provide the breathing pattern sensory data to a user computing entity 20 and/or a management computing entity 10. The user computing entity 20 and and/or management computing entity 10 may process and/or analyze the breathing pattern sensory data to identify any splinting points reflected therein. The results of the analysis and/or processing of the breathing pattern sensory data may be stored (e.g., in memory) by the user computing entity 20 and/or the management computing entity 10. In an example embodiment, the user computing entity 20 and/or management computing entity 10 may also store and/or provide the breathing pattern sensory data.

In another example embodiment, the breathing monitoring device 40 may capture breathing pattern sensory data; process and/or analyze the breathing pattern sensory data to identify any splinting points reflected therein; and store and/or provide the breathing pattern sensory data and/or processing of the breathing pattern sensory data. A user computing entity 20 and/or a management computing entity 10 may receive and/or provide the breathing pattern sensory data, results of the analysis and/or processing of the breathing pattern sensory data, and store and/or provide at least a portion of the received information for review by a physician and/or other healthcare worker (e.g., via a user interface).

In various embodiments, a stimulator apparatus 60 comprising one or more transmitters 602 is positioned with respect to the monitored individual's body (e.g., worn by the monitored individual). As noted above, the stimulator apparatus 60 may be embodied as a wearable device, such as a glove, having the one or more transmitters 602 integrated therein and/or secured thereto. For example, the stimulator apparatus 60 may comprise one or more transmitters 602 configured for emitting stimulation signals to a nerve of the monitored individual.

In various embodiments, the stimulator apparatus 60 may be in communication with a user computing entity 20, a management computing entity 10, a breathing monitoring device 40, and/or a network 30. In various embodiments, a management computing entity 10 may cause operation of the stimulator apparatus 60 (e.g., causing the stimulator apparatus 60 to emit a stimulation signal). For example, the management computing entity 10 may be configured and/or programmed to control one or more functions of a stimulator apparatus 60 in communication with the management computing entity 10. Particularly, the management computing entity 10 may cause the stimulator apparatus 60 to apply (e.g., transmit) a stimulation signal at an instance corresponding to (coextensive with) a splinting point in the inspiration of the monitored individual, such that the stimulation is applied simultaneously with an expected time period during which the patient experiences pain or discomfort that would otherwise lead to splinting. The timing of the application of the stimulation signal may vary, such as to begin application of the stimulation shortly before (e.g., 500 msec before) an expected time at which the patient is likely to begin experiencing pain or discomfort during a breathing cycle.

In some embodiments, the stimulator apparatus 60 may be in wired or wireless communication with a user computing entity 20 (e.g., co-located, for example within the same room as the stimulator apparatus 60). In the noted embodiments, a user computing entity 20 may operate a monitoring application (e.g., stored in memory 322, 324 and executed by processing element 308) that may be configured and/or programmed to control one or more functions of a stimulator apparatus 60 in communication with the user computing entity 20. Particularly, the user computing entity 20 may cause the stimulator apparatus 60 to apply (e.g., transmit) a stimulation signal at an instance corresponding to (coextensive with) a splinting point in the inspiration of the monitored individual, such that the stimulation is applied simultaneously with an expected time period during which the patient experiences pain or discomfort that would otherwise lead to splinting. The timing of the application of the stimulation signal may vary, such as to begin application of the stimulation shortly before (e.g., 500 msec before) an expected time at which the patient is likely to begin experiencing pain or discomfort during a breathing cycle.

Thus, in various embodiments, a user computing entity 20 and/or a management computing entity 10 may control a breathing monitoring device 40 and/or a stimulator apparatus 60. In various embodiments the breathing monitoring device 40 is a standalone, and possibly dedicated, device that may be configured to communicate information/data to/from a user computer entity 20 and/or management computer entity 10 and/or stimulator apparatus 60.

Exemplary Breathing Monitoring Process

Figure 7:
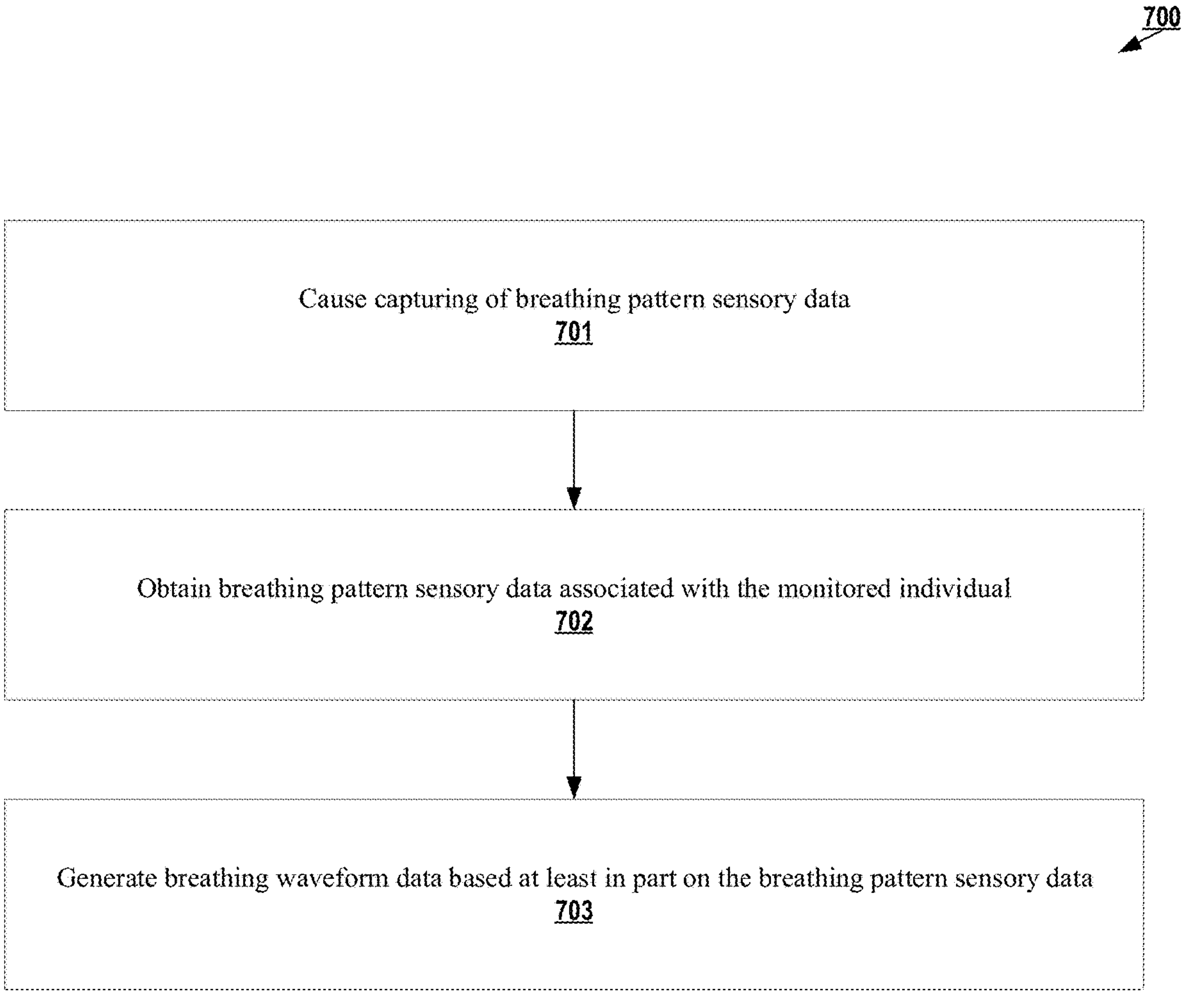
FIG. 7 is a flow chart illustrating an examples process for conducting a breathing monitoring session, in accordance with certain embodiments.

FIG. 7 provides a flowchart illustrating example operations for conducting a breathing monitoring session (e.g., therapy session) to determine the breathing pattern and to thereby generate breathing pattern sensory data of a monitored individual (patient) with respect to an inspiration and expiration cycle of the monitored individual and to determine if any splinting points are reflected therein. FIG. 7 is discussed with reference to the processing and analysis of the breathing pattern sensory data being processed by the management computing entity 10. However, as noted above, the user computing entity 20 and/or breathing monitoring device 40 may be configured to process and analyze the captured breathing pattern sensory data.

With reference to FIG. 7, a method for monitoring the breathing pattern of a patient begins by adhering the breathing monitoring device 40 to the monitored individual and obtaining breathing pattern sensory data as indicated in step/operation 701, as well as positioning the stimulator apparatus 60 on the monitored individual's hand (e.g., worn). At step operation 701, a breathing monitoring session (e.g., therapy session) may begin by positioning one or more sensors of the breathing monitoring device 40 on the diaphragm (or chest) region of the monitored individual and providing input (e.g., by the management computing entity 10) to the breathing monitoring device 40 (e.g., via input/output circuitry) that a monitoring session should be conducted. For example, as noted above, the breathing monitoring device 40 may be embodied as a wearable device, such as an adhesive-style device that may be adhered to a patient's skin, that may be positioned on the monitored individual so as to cause the one or more sensors integrated into and/or secured to the wearable device to be properly positioned with respect to the monitored individual's diaphragm (or chest) region.

Once the one or more sensors are properly positioned with respect to the monitored individual's chest (or diaphragm) and the input indicating a monitoring session should be conducted is received, the breathing monitoring device 40 may control (e.g., via controller 404), the one or more sensors to capture breathing pattern sensory data for the monitored individual with respect to a breathing cycle, and provide the breathing pattern sensory data to the management computing entity 10. The breathing monitoring device 40 may provide the breathing pattern sensory data such that the processing element 205 of the management computing entity 10 obtains the breathing pattern sensory data.

In various embodiments, breathing pattern sensory data comprise breathing measurements reflecting the expansion and contraction of the diaphragm (and/or rise and fall of the chest) of the monitored individual as the monitored individual breathes through periods of inspiration and expiration during a breathing cycle. In various embodiments, the breathing pattern sensory data may be represented by a signal (e.g., voltage signal) or other digitized signal generated by the one or more sensors (e.g., stretch sensor) corresponding to a breathing cycle of the monitored individual. In example embodiments, breathing pattern sensory data may be associated with metadata such as patient identifier identifying the monitored individual (e.g., name); a date and/or time at which the breathing pattern sensory data were captured; information/data corresponding to the location of the one or more sensors on the monitored individual's body (e.g., chest, diaphragm, and/or the like); information/data corresponding to the patient's body position (e.g., sitting, standing, and/or the like), information/data corresponding to the patient's breathing manner (e.g., rapid breathing, slow breathing, and/or the like), information/data corresponding to the patient's movement (e.g., stationary, walking, and/or the like); an electronic health record corresponding to the monitored individual, and/or the like.

At step/operation 702, the management computing entity 10 obtains the breathing pattern sensory data associated with the monitored individual. For example, as noted above, the controller 404 of the breathing monitoring device may obtain (e.g., collect) breathing pattern sensory data via one or more sensors 401 for an initial time period (e.g., a breathing cycle) and generate and transmit at least a portion of the obtained breathing pattern sensory data to the management computing entity 10. The management computing entity 10 may store the breathing pattern sensory data in conjunction with a user profile.

At step/operation 703, the management computing entity 10 generates breathing waveform data based at least in part on the breathing pattern sensory data. Breathing waveform data may reflect a breathing cycle of inspiration and expiration of the monitored individual. For example, the breathing waveform data may describe a graphical representation of the inspiration pattern and expiration pattern of a breathing cycle of the monitored individual.

Figure 8C:
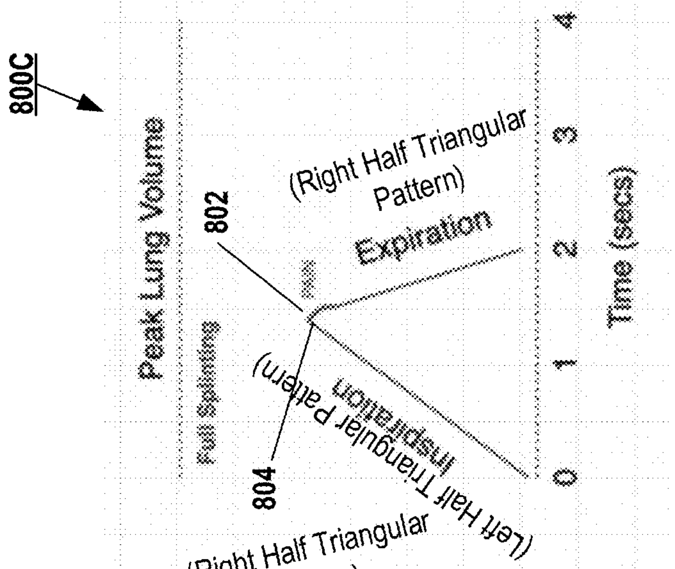
FIGS. 8A-8C provide operational examples of breathing waveform data in accordance with certain embodiments.
Figure 8B:
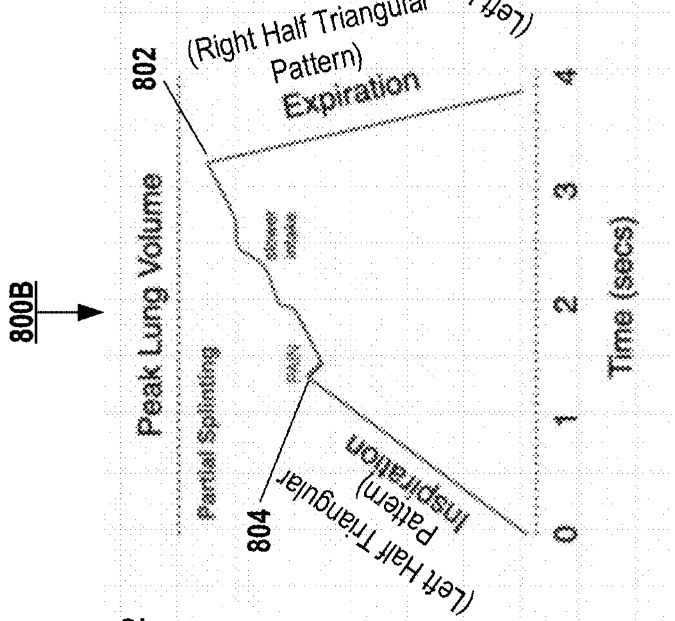
Figure 8A:
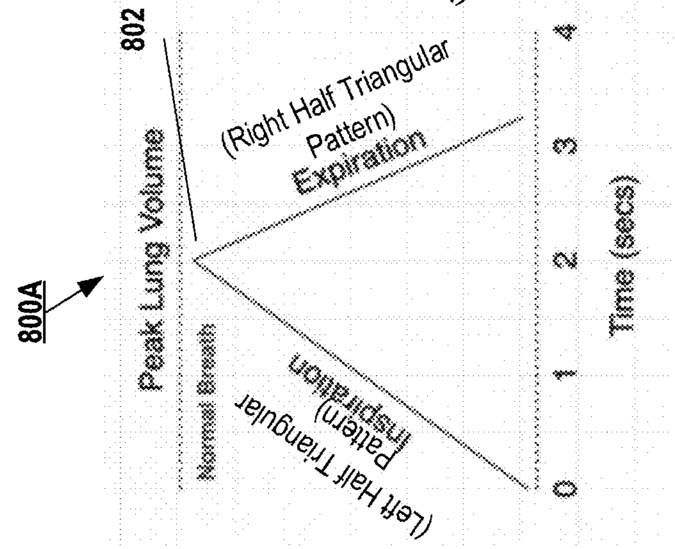

Operational examples of breathing waveform data are depicted in FIGS. 8A-8C. FIG. 8A depicts breathing waveform data 800A for breathing pattern sensory data reflecting normal breath (e.g., expected breathing waveform data). FIG. 8B depicts breathing waveform data 800B for breathing pattern sensory data reflecting partial splinting. FIG. 8C depicts breathing waveform data 800C for breathing pattern sensory data reflecting full splinting. Breathing waveform data describes a graphical representation/depiction (e.g., periodic wave pattern) of a breathing cycle of a monitored individual defined by an upward trajectory (during inhalation) and ending at a peak defining full lung capacity, and a downward trajectory (during exhalation) defining a minimum/trough for empty lung capacity. The graphical representation may be at least substantially triangular, substantially hyperbolic, and/or the like. As an example, the operation examples of breathing waveform data of FIGS. 8A-8C define a substantially triangular pattern on a graphical depiction of the patient's breathing, with the x-axis (horizontal axis) representing time (in seconds) from the beginning of inspiration through and to the end of expiration of the breathing cycle, and the y-axis (vertical axis) representing lung volume. In the graphical depictions of FIGS. 8A-8C, the substantially triangular pattern may define a left half triangular pattern that is associated with a detected inspiration pattern for the breathing pattern sensory data. For example, the left half triangular pattern may describe an upward trajectory that corresponds to the inspiration pattern for the breathing pattern sensory data of the monitored individual. Additionally, the substantially triangular pattern may define a right half triangular pattern that is associated with a detected expiration pattern for the breathing pattern sensory data.

As depicted in FIGS. 8A-8C, breathing waveform data (e.g., graphical depiction) may be characterized by one or more attributes. Particularly, breathing waveform data may describe: (i) a peak inspiration 802 reflected within the breathing waveform data (e.g., maximum point in the upward trajectory reflecting volume of breath intake of the patient during the breathing cycle); (ii) a time from the beginning of inspiration reflected within the breathing waveform data to the peak inspiration reflected within the breathing waveform pattern, and/or (iii) a time from the beginning of inspiration reflected within the breathing waveform data to an interruption 804 in the upward trajectory of the inspiration pattern as depicted in FIGS. 8B-8C.

Exemplary Detection of Splinting Points

Figure 9:
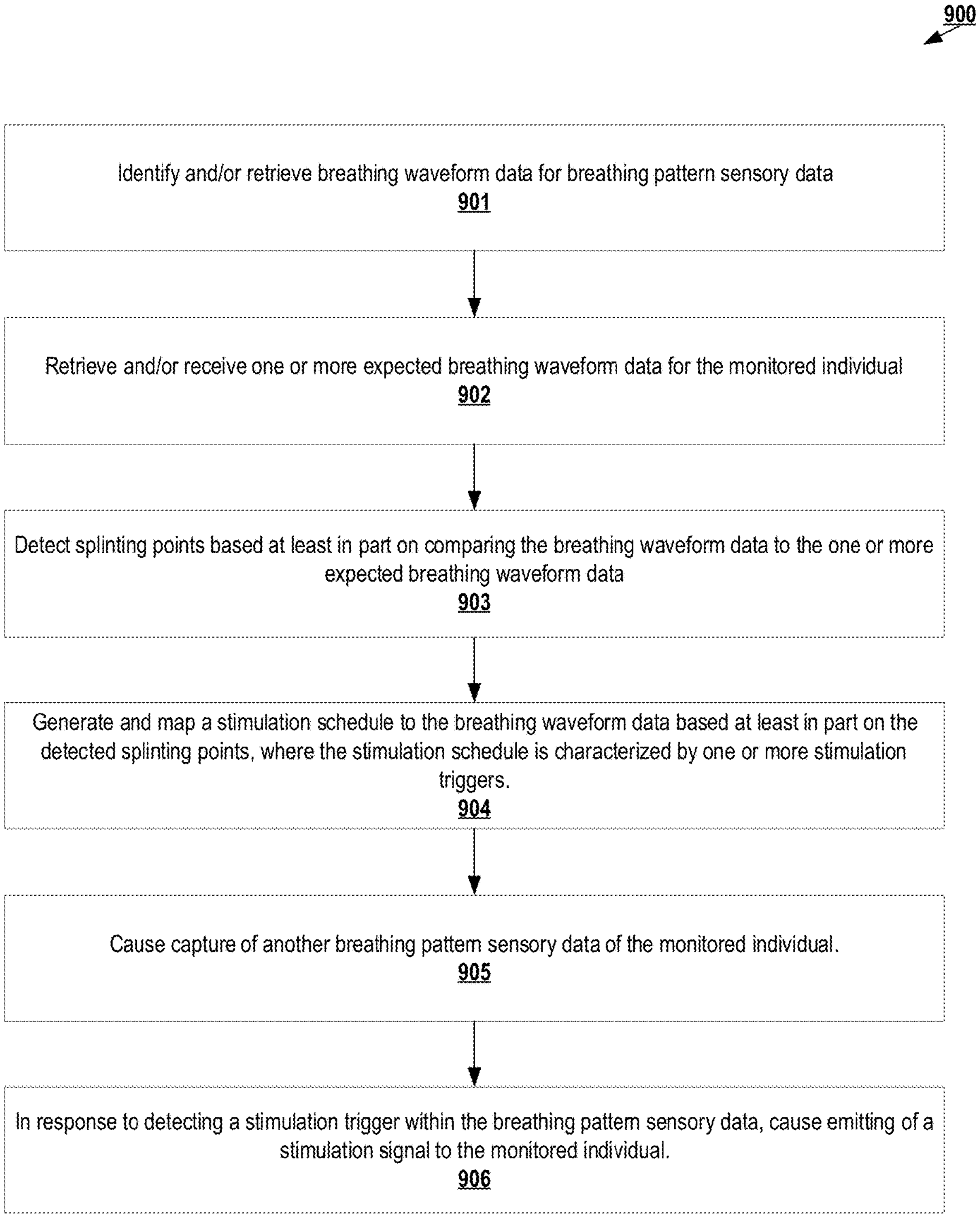
FIG. 9 is a flowchart illustrating an example process for detecting splinting and identifying splinting points, in accordance with certain embodiments.

FIG. 9 provides a flowchart illustrating example operations for detecting splinting and identifying splinting points reflected within breathing waveform data reflecting a breathing cycle of inspiration and expiration of a monitored individual. FIG. 9 continues the process of FIG. 7 where breathing waveform data was generated. In the process of FIG. 9, the breathing waveform data is processed and/or analyzed to determine (e.g. detect) whether splinting is reflected within the breathing waveform data and to identify splinting points if splinting is detected. In an example embodiment, at least a portion of the processing and/or analyzing the breathing waveform data is performed using the processing element 205 of the management computing entity 10.

In various embodiments, the breathing waveform data is processed and/or analyzed utilizing a machine learning model. For example, a machine learning-trained model may receive the breathing waveform data as input and process the breathing waveform data to detect splinting and corresponding splinting points. In certain embodiments, the machine learning model outputs a score (e.g., a predicted interruption score discussed in detail below) that indicates whether splinting is reflected within the breathing waveform data. For example, the score may be a Boolean value (e.g., where a one-valued predicted interruption score may represent that splinting is reflected within a corresponding breathing waveform data, while a zero-valued predicted interruption score may represent that splinting is not reflected within the corresponding breathing waveform data).

In some embodiments, the machine learning model utilizes one or more expected breathing waveform data in processing and/or analyzing the breathing waveform data (e.g., current breathing waveform data). FIG. 8A described above depicts an operational example of expected breathing waveform data. Expected breathing waveform data describes a normal breathing pattern (full breath) of a monitored individual with respect to a breathing cycle of the monitored individual. Particularly, expected breathing waveform data reflects a breathing cycle without splinting in the inspiration portion of the breathing cycle. In example embodiments, expected breathing waveform data may be generated by processing breathing pattern sensory data measured/captured (or otherwise collected) during one or more breathing cycles (e.g., inspiration and expiration cycles) of the monitored individual, where splinting is not reflected in the breathing pattern sensory data. In some embodiments, the breathing pattern sensory data may be captured under the supervision of a physician, clinician, and/or the like. For example, in some embodiments, the monitored individual may be guided through one or more breathing cycles to capture one or more breathing pattern sensory data that are in turn used to generate one or more breathing waveform data for the monitored individual. In some embodiments, the one or more breathing waveform data may comprise breathing waveform data reflecting maximum breath of the monitored individual, breathing waveform data reflecting minimum breath of the monitored individual, and/or breathing waveform data reflecting normal breath of the monitored individual. In various embodiments, the machine learning model may be configured to learn minimum breath and/or maximum breath reflected in breathing pattern sensory data and/or breathing waveform data across a time period (e.g., 12 hours, one day, one week, and/or the like).

In certain embodiments, expected breathing waveform data is generated, utilizing a machine learning model, based at least in part on one or more breathing pattern sensory data and/or breathing waveform data of other individuals. For example, in some embodiments, the machine learning model may be trained using supervised machine-learning techniques, using training data reflecting breathing pattern of certain individuals, where the certain individuals may be individuals that have certain similarities as the monitored individual. As an example, the similarities may be similarities in size, environment, activities, medical conditions, medical records, and/or the like.

In various embodiments, the training data may comprise breathing pattern sensory data and/or breathing waveform data of the certain individuals. In some embodiments the training data may comprise (i) breathing pattern sensory data and/or breathing waveform data reflecting maximum breath (e.g., lungs full) of one or more of the certain individuals, (ii) breathing pattern sensory data and/or breathing waveform data reflecting minimum breath (e.g., lungs empty) of one or more of the certain individuals, and/or (iii) breathing pattern sensory data and/or breathing waveform data reflecting normal breath of one or more of the certain individuals. In various embodiments, the machine learning model may be configured to learn minimum breath and/or maximum breath reflected in breathing pattern sensory data and/or breathing waveform data across a time period (e.g., 12 hours, one day, one week, and/or the like).

In various embodiments, data reflecting breathing pattern of the certain individuals may be utilized as input to the machine learning model. The machine learning model may be configured to output one or more expected breathing waveform data of the monitored individual. In some embodiments, the machine learning model may be configured to correlate an average for the monitored individual to determine expected breathing waveform data. In various embodiments, the training data may reflect a breathing pattern of one or more distressed individuals (e.g., individuals that experience splinting during breathing). The machine learning model may be configured to identify, utilizing the training data reflecting breathing pattern of the one or more distressed individuals, common patterns and adjust expectations due to data (e.g., machine learning data) reflecting successful treatment (e.g., improved breathing, breathing without splinting, and/or the like) of the monitored individual.

With reference to FIG. 9, a method for detecting splinting and corresponding splinting points reflected within breathing waveform data, utilizing a machine learning model begins at step/operation 901. At step/operation 901, the management computing entity 10 identifies and/or retrieves (e.g., from memory 210, 215) breathing waveform data for breathing pattern sensory data captured using the breathing monitoring device 40 as described with reference to FIG. 7 (steps/operations 701-703).

At step/operation 902, the management computing entity 10, identifies one or more expected breathing waveform data (discussed in detail below). In some embodiments, the management computing entity 10 retrieves the one or more expected breathing waveform data from a memory (e.g., memory 210, 215) of the management computing entity 10. In certain embodiments, the management computing entity receives the one or more expected breathing waveform data from another computing entity (e.g., user computing entity 20).

At step/operation 903, the management computing entity 10, utilizing a machine learning model, determines whether splinting is reflected within the breathing waveform data based at least in part on comparing the breathing waveform data to the one or more expected breathing waveform data. In various embodiments, the machine learning model is configured to take as input the breathing waveform data (reflecting the monitored individual's actual breathing pattern); analyze and/or process the breathing waveform data by comparing the breathing waveform data to the one or more expected breathing waveform data for the monitored individual; and output data that indicates whether splinting is reflected within the breathing waveform data and/or data that indicates the splinting points within the breathing waveform data (if splinting is detected).

In some embodiments, comparing breathing waveform data to expected breathing waveform data of the one or more expected breathing waveform data comprise comparing one or more attributes of the breathing waveform data to one or more similar (e.g., same) attributes of the expected breathing waveform data. As an example, in some embodiments, when comparing breathing waveform data to expected breathing waveform data, the management computing entity 10 (e.g., utilizing the machine learning model) compares the peak inspiration reflected within the breathing waveform data to the peak inspiration reflected within the expected breathing waveform data and determines a difference measure for the breathing waveform data and the expected breathing waveform data. As another example, in some embodiments, when comparing breathing waveform data to expected breathing waveform data, the management computing entity 10 (e.g., utilizing the machine learning model) compares a time from the beginning of inspiration reflected within the breathing waveform data to the peak inspiration reflected within the breathing waveform data to a time from the beginning of inspiration reflected within the expected breathing waveform data to the peak inspiration reflected within the expected breathing waveform data and determines a difference measure between the times for the breathing waveform data and the expected breathing waveform data.

As yet another example, in some embodiments, when comparing the breathing waveform data to expected breathing waveform data, the management computing entity 10 (e.g., utilizing the machine learning model) compares a ratio of time from the beginning of inspiration reflected within the breathing waveform data to the peak inspiration reflected within the breathing waveform data to a ratio of time from the beginning of inspiration reflected within the expected breathing waveform data to the peak inspiration reflected within the expected breathing waveform data and determines a difference measure between the two ratios for the breathing waveform data and the expected breathing waveform data. As a further example, in some embodiments, when comparing breathing waveform data to expected breathing waveform data, the management computing entity 10 (e.g., utilizing the machine learning model) compares a portion of the breathing waveform data reflecting inspiration to a portion of the expected breathing waveform data reflecting inspiration and determines a difference measure between the portions for the breathing waveform data and the expected breathing waveform data, where the difference measure may be indicative of patches, hitches and/or other interruptions (e.g., splinting) in the inspiration of the monitored individual reflected within the breathing waveform data.

As yet further example, in some embodiments, when comparing breathing waveform data to expected breathing waveform data, the management computing entity 10 (e.g., utilizing the machine learning model) compares one or more of: (i) the peak inspiration reflected within the breathing waveform data to the peak inspiration reflected within the expected breathing waveform data, (ii) a time from the beginning of inspiration reflected within the breathing waveform data to the peak inspiration reflected within the breathing waveform data to a time from the beginning of inspiration reflected within the expected breathing waveform data to the peak inspiration reflected within the expected breathing waveform data, (iii) a ratio of time from the beginning of inspiration reflected within the breathing waveform data to the peak inspiration reflected within the breathing waveform data to a ratio of time from the beginning of inspiration reflected within the expected breathing waveform data to the peak inspiration reflected within the expected breathing waveform data, and (iv) a portion of the breathing waveform data reflecting inspiration to a portion of the expected breathing waveform data reflecting inspiration.

In some embodiments, comparing breathing waveform data to expected breathing waveform data may comprise identifying one or more of: (i) a brief pause in the inspiration of the monitored individual reflected in the breathing waveform data (e.g., just before a splinting point, at a splinting point, and/or the like) but not reflected in the expected breathing waveform data, (ii) an acceleration in the inspiration of the monitored individual reflected in the breathing waveform data but not reflected in the expected breathing waveform data, (iii) a deceleration in the inspiration of the monitored individual reflected in the breathing waveform data but not reflected in the expected breathing waveform data, (iv) a series of pauses in the inspiration of the monitored individual (e.g., followed by continued inspiration) reflected in the breathing waveform data but not reflected in the expected breathing waveform data, and/or (v) pauses between breaths reflected in the breathing waveform data but not reflected in the expected breathing waveform data. Pauses between breaths may be indicative of severe splinting.

Figure 10:
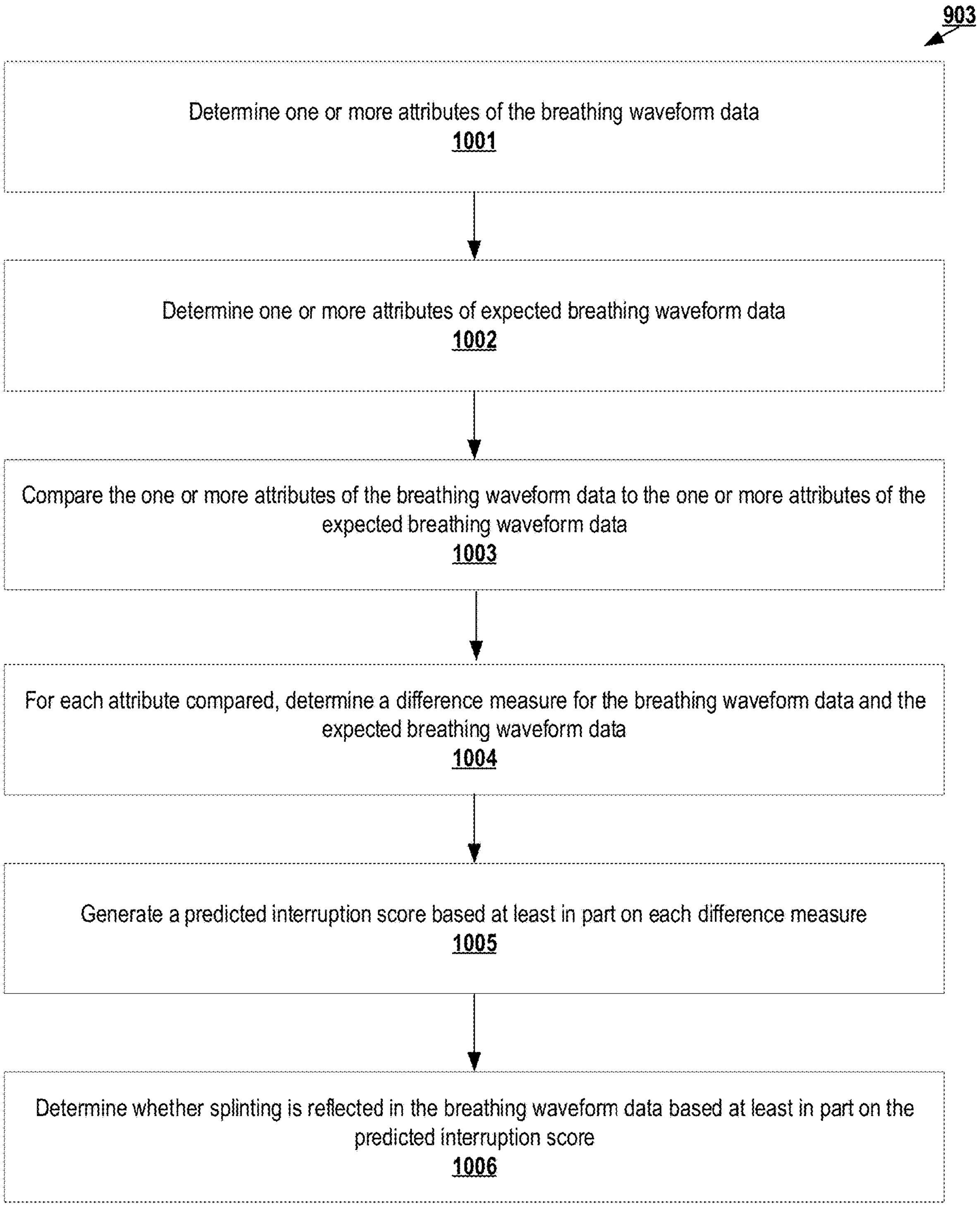
FIG. 10 is a flowchart illustrating an example process for detecting whether splinting is reflected within breathing waveform data utilizing a machine learning model, in accordance with certain embodiment.

In some embodiments, the step/operation 903 may be performed in accordance with the process that is depicted in FIG. 10. The process that is depicted in FIG. 10 begins at step/operation 1001 when the management computing entity 10 determines one or more attributes of the breathing waveform data. In certain embodiments, the management computing entity 10 identifies one or more of: (i) a peak inspiration reflected within the breathing waveform data; (ii) a time from the beginning of inspiration reflected within the breathing waveform data to the peak inspiration reflected within the breathing waveform data; (iii) a ratio of time from the beginning of inspiration reflected within the breathing waveform data to the peak inspiration reflected within the breathing waveform data; and (iv) a portion of the breathing waveform data reflecting inspiration The process continues at step/operation 1002, when the management computing entity 10 determines one or more attributes (e.g., same attributes as that of the breathing waveform data) of a corresponding expected breathing waveform data. Accordingly, in certain embodiments, the management computing entity 10 identifies one or more of: (i) the peak inspiration reflected within the expected breathing waveform data; (ii) a time from the beginning of inspiration reflected within the expected breathing waveform data to the peak inspiration reflected within the expected breathing waveform data; (iii) a ratio of time from the beginning of inspiration reflected within the expected breathing waveform data to the peak inspiration reflected within the expected breathing waveform data; and (iv) a portion of the expected breathing waveform data reflecting inspiration.

At step/operation 1003, the management computing entity 10 compares the one or more attributes of the breathing waveform data to the one or more attributes of the expected breathing waveform data. For example, in certain embodiments, the management computing entity compares the peak inspiration reflected within the breathing waveform data to the peak inspiration reflected within the expected breathing waveform data and/or compares a time from the beginning of inspiration reflected within the breathing waveform data to the peak inspiration reflected within the breathing waveform data to a time from the beginning of inspiration reflected within the expected breathing waveform data to the peak inspiration reflected within the expected breathing waveform data and/or compares a ratio of time from the beginning of inspiration reflected within the breathing waveform data to the peak inspiration reflected within the breathing waveform data to a ratio of time from the beginning of inspiration reflected within the expected breathing waveform data to the peak inspiration reflected within the expected breathing waveform data and/or compares a portion of the breathing waveform data reflecting inspiration to a portion of the expected breathing waveform data reflecting inspiration.

At step/operation 1004, for each attribute of the breathing waveform data and the expected breathing waveform data compared, the management computing entity 10 determines a difference measure for the breathing waveform data and the expected breathing waveform data. In some embodiments, the management computing entity 10 may compare the breathing waveform data to a plurality of expected breathing waveform data. At step/operation 1005, the management computing entity 10 generates a predicted interruption score based at least in part on each of the difference measures. In certain embodiments, generating a predicted interruption score based at least in part on each difference measure comprise determining whether a difference measure satisfies a difference measure threshold. In some embodiments, the management computing entity 10 generates the predicted interruption score based at least in part on whether a lowest difference measure associated with the breathing waveform data satisfies a difference measure threshold.

At step/operation 1006, the management computing entity 10 determines whether splinting is reflected within the breathing waveform data based at least in part on the predicted interruption score. In certain embodiments the machine learning model is configured to output a Boolean value, where a one-valued predicted interruption score represents that splinting is reflected within a corresponding breathing waveform data, while a zero-valued predicted interruption score represents that splinting is not reflected within the corresponding breathing waveform data. In certain embodiments, the machine learning model is configured to output a vector comprising data representing a location of splinting (splinting point) as reflected within the breathing waveform data. In the noted embodiments, each splinting point may be associated with an occurrence timestamp (e.g., each splinting occurrence reflected within the breathing waveform data may be associated with an occurrence time-stamp), where an occurrence timestamp describes a duration from the beginning of inspiration (reference point) to a splinting point in the inspiration.

Returning to FIG. 9, when at step/operation 903, it is determined that splinting is reflected in the breathing wave-form data based at least in part on comparing the breathing waveform data to one or more expected breathing waveform data, the process continues at step operation 904. At step/operation 904, the management computing entity 10 generates and maps a stimulation schedule to the breathing waveform data based at least in part on the detected splinting points reflected within the breathing waveform data.

Mapping a stimulation schedule encompasses defining one or more stimulation triggers and corresponding emit timestamp for each stimulation trigger of the one more stimulation triggers, where the one or more stimulation triggers may be reflected within the breathing waveform data and may be detectable within the breathing pattern sensory data. Defining the one or more stimulation triggers and associated emit timestamp comprise generating a stimulation trigger for each detected splinting point, and for each stimulation trigger determining an emit timestamp based at least in part on an occurrence timestamp associated with the corresponding splinting point. Thus, each stimulation trigger is associated with a detected splinting point. As noted above, an occurrence timestamp describes a duration from the beginning of inspiration (e.g., reference point) to a detected splinting point in inspiration. In certain embodiments, an emit timestamp is temporally aligned with a corresponding occurrence timestamp such that the emit timestamp describes a duration from the beginning of inspiration to a corresponding detected splinting point. In certain embodiments, an emit timestamp describes a duration from the beginning of inspiration to shortly before (e.g., 500 msec before) a corresponding detected splinting point.

Figure 11:
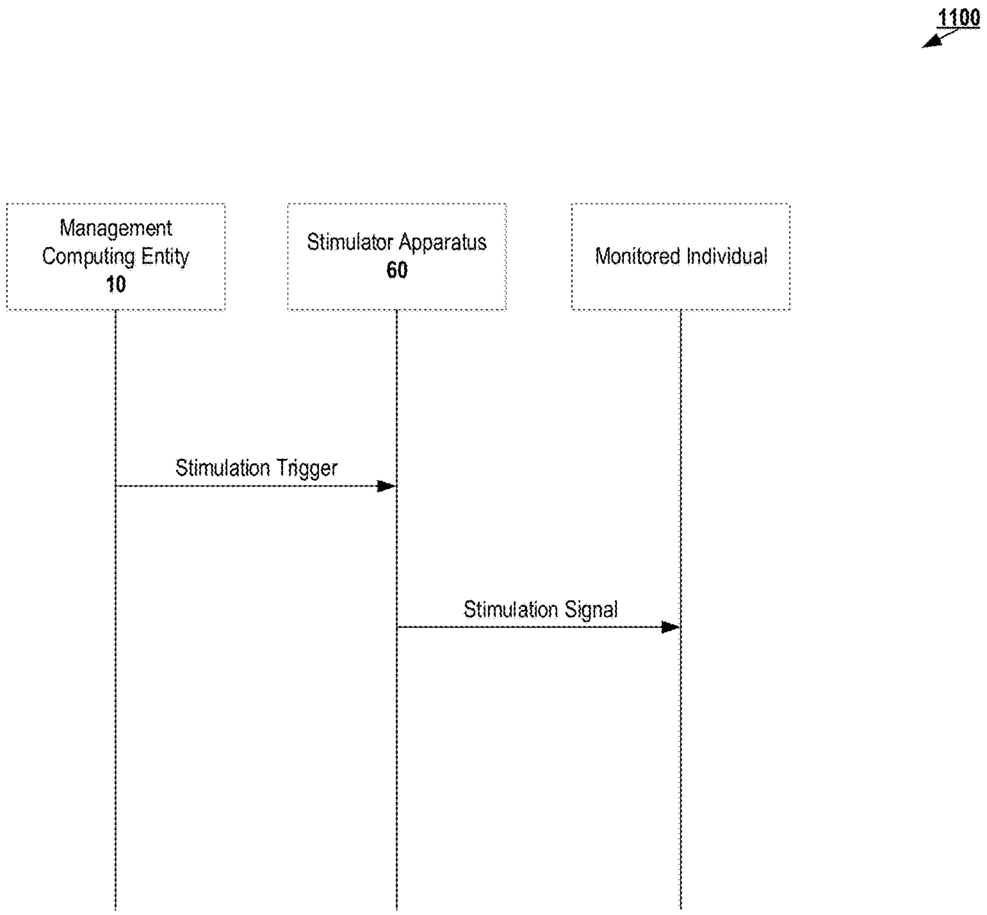
FIG. 11 is a signal diagram of an example process of implementing a stimulation schedule to the patient's body in accordance with certain embodiments.

Each stimulation trigger is configured to trigger the stimulator apparatus to transmit a stimulation signal to the monitored individual at the associated emit timestamp based at least in part on input from the management computing entity 10. FIG. 11 is a signal diagram reflecting an example process of implementing a stimulation schedule to provide stimulation signals to the patient's body (e.g., patient's hand). As depicted in FIG. 11, the management computing entity 10 triggers the stimulator apparatus 60 to transmit a stimulation signal and in response, the stimulator apparatus 60 transmits a stimulation signal to the monitored individual. In the example embodiment of FIG. 11, the management computing entity 10 triggers the stimulator apparatus 60 to transmit a stimulation signal, however, in certain embodiments, the user computing entity 20 may be configured to trigger the stimulator apparatus 60 to transmit a stimulation signal.

A stimulation signal is characterized by one or more stimulation parameters (e.g., intensity level, stimulation duration, pulse duration, pulse width, and/or the like). The determination of an appropriate level of intensity is necessary to efficiently and effectively assist the monitored individual breathe through a splinting point (e.g., by providing adequate stimulation to lessen pain in the lungs and/or at least partially distract the patient's nervous system into not noticing the pain). The intensity of a signal is defined based at least in part on the transmitter 602 utilized to apply the signal. For electrical pulse generators, the intensity may be defined based at least in part on the voltage and/or current applied (e.g., in micro-volts, milliamps, or other unit as relevant to the operation of the electrical pulse generator). For vibrators, the intensity may be defined based at least in part on the level of intensity of vibration applied (which may be measured based at least in part on the amount of electrical current applied across the mechanical vibration element within the vibration generator). For pressure generators, the intensity may be defined based at least in part on the amount of displacement of an actuator pressed into the patient's skin or frequency that the actuator is pressed into the patient's skin, or force applied to the patient's skin (e.g., a higher displacement into the patient's skin/higher force correlated to a higher intensity).

In some embodiments, the determination of an appropriate level of intensity may be provided through a process of applying a series of stimulation signals (e.g., signal pulses) to the monitored individual's body (e.g., target nerve) with those signal pulses being applied at different intensity levels (e.g., starting at an initial intensity level and increasing the intensity level) and determining an appropriate stimulation signal based at least in part on the ability of the monitored individual to breathe through a detected splinting point (e.g., due to the transmitted stimulation signal). The ability of the monitored individual to breathe through a detected splinting point may be determined by capturing real-time breathing pattern sensory data for the monitored individual, generating breathing waveform data, and analyzing the breathing wave-form data to determine if splinting is reflected within the breathing waveform data.

For example, the management computing entity 10 may cause the stimulator apparatus 60 to transmit an initial stimulation signal with a first intensity level (e.g., prescribed by a physician and/or the like) at an emit timestamp corresponding to a detected splinting point in the inspiration of the monitored individual. The management computing entity 10 may then generate breathing waveform data based at least in part on breathing pattern sensory data captured by the breathing monitoring device 40 during the breathing cycle of the monitored individual and analyze the breathing waveform data to determine whether splinting is still reflected therein. If splinting is still detected, the process is repeated but with an increased intensity level. This process may be repeated multiple times, with an increased intensity level each time until splinting is not detected (or splinting is detected to be decreased). The stimulator apparatus 60 may be capable of implementing a maximum intensity level (at a level that is not harmful to the monitored individual), such that the intensity level is not increased beyond the maximum intensity level even if the stimulation intensity does not impact the patient's splinting.

Returning to FIG. 9, at step/operation 905, the management computing entity 10 causes the breathing monitoring device 40 to capture another breathing pattern sensory data of the monitored individual. At step/operation 906, in response to detecting a stimulation trigger of the one or more stimulation triggers within the breathing pattern sensory data, the management computing entity 10 causes the stimulator apparatus 60 to emit a stimulation signal to the monitored individual at the associated emit timestamp so as to assist the monitored individual breathe through the pain (e.g., by providing adequate stimulation to lessen pain in the lungs and/or at least partially distract the patient's nervous system into not noticing the pain).

CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented method comprising:

receiving, by one or more processors, breathing pattern sensory data generated based at least in part on output of a breathing sensor monitoring a breathing of a monitored individual;

generating, by the one or more processors, breathing waveform data reflecting a breathing cycle of the monitored individual comprising an actual inspiration portion and an actual expiration portion, based at least in part on the breathing pattern sensory data for the monitored individual;

determining, by the one or more processors, a splinting occurrence reflected within the breathing waveform data, wherein;

(i) the splinting occurrence is defined by a shortened inspiration portion of the breathing cycle relative to an expected inspiration portion of an expected breathing waveform for the monitored individual, and (ii) the shortened inspiration portion of the breathing cycle is determined based on a difference measure between (a) a measured time between an actual start of the actual inspiration portion and an actual peak of the actual inspiration portion and (b) an expected time between an expected start of the expected inspiration portion and an expected peak of the expected inspiration portion;

in response to the splinting occurrence, mapping, by the one or more processors, a stimulation schedule to the breathing waveform data, wherein the stimulation schedule defines a plurality of stimulation triggers reflected within the breathing waveform data and detectable within the breathing pattern sensory data for stimulating nerves of the monitored individual; and in response to detecting a stimulation trigger of the plurality of stimulation triggers within the breathing pattern sensory data, causing, by the one or more processors, a stimulator configured to be in contact with the monitored individual to emit a stimulation signal to the monitored individual, wherein the stimulation signal is characterized by stimulation parameters.

2. The computer-implemented method of claim 1, wherein determining the splinting occurrence comprises identifying a location within the breathing waveform data reflecting a difference between the breathing waveform data and the expected breathing waveform.

3. The computer-implemented method of claim 1, wherein (i) the splinting occurrence is associated with an occurrence timestamp and (ii) the stimulation trigger is associated with an emit timestamp that is temporally aligned with the occurrence timestamp.

4. The computer-implemented method of claim 3, wherein causing the stimulator configured to be in contact with the monitored individual to emit the stimulation signal to the monitored individual comprises:

causing the stimulator to emit the stimulation signal at an instance corresponding to the emit timestamp associated with the stimulation trigger.

5. The computer-implemented method of claim 1, wherein causing the stimulator to emit the stimulation signal to the monitored individual comprises:

causing the stimulator to emit the stimulation signal embodied as one of: an electrical pulse, a vibration, or a heat signal.

6. The computer-implemented method of claim 1, wherein the stimulation parameters comprise one or more of: an intensity level, a pulse width, and a pulse duration.

7. The computer-implemented method of claim 1, wherein determining the splinting occurrence comprises:

comparing, using a machine learning model, the breathing waveform data to the expected breathing waveform.

8. The computer-implemented method of claim 1, wherein causing the stimulator configured to be in contact with the monitored individual to emit the stimulation signal to the monitored individual comprises:

causing the stimulator to emit the stimulation signal to a region of the monitored individual.

9. The computer-implemented method of claim 1, wherein the shortened inspiration portion of the breathing cycle is determined based on the difference measure satisfying a difference measure threshold.

10. A system comprising:

one or more processors; and at least one memory storing processor-executable instructions that, when executed by the one or more processors, cause the one or more processors to:

receive breathing pattern sensory data generated based at least in part on output of a breathing sensor monitoring a breathing of a monitored individual;

generate breathing waveform data reflecting a breathing cycle of the monitored individual comprising an actual inspiration portion and an actual expiration portion, based at least in part on the breathing pattern sensory data for the monitored individual;

determine a splinting occurrence reflected within the breathing waveform data, wherein:

(i) the splinting occurrence is defined by a shortened inspiration portion of the breathing cycle relative to an expected inspiration portion of an expected breathing waveform for the monitored individual, and (ii) the shortened inspiration portion of the breathing cycle is determined based on a difference measure between (a) a measured time between an actual start of the actual inspiration portion and an actual peak of the actual inspiration portion and (b) an expected time between an expected start of the expected inspiration portion and an expected peak of the expected inspiration portion;

in response to the splinting occurrence, map a stimulation schedule to the breathing waveform data, wherein the stimulation schedule defines a plurality of stimulation triggers reflected within the breathing waveform data and detectable within the breathing pattern sensory data for stimulating nerves of the monitored individual; and in response to detecting a stimulation trigger of the plurality of stimulation triggers within the breathing pattern sensory data, cause a stimulator configured to be in contact with the monitored individual to emit a stimulation signal to the monitored individual, wherein the stimulation signal is characterized by stimulation parameters.

11. The system of claim 10, wherein determining the splinting occurrence comprises identifying a location within the breathing waveform data reflecting a difference between the breathing waveform data and the expected breathing waveform.

12. The system of claim 10, wherein (i) the splinting occurrence is associated with an occurrence timestamp and (ii) the stimulation trigger is associated with an emit timestamp that is temporally aligned with the occurrence timestamp.

13. The system of claim 12, wherein causing the stimulator configured to be in contact with the monitored individual to emit the stimulation signal to the monitored individual comprises:

causing the stimulator to emit the stimulation signal at an instance corresponding to the emit timestamp associated with the stimulation trigger.

14. The system of claim 10, wherein causing the stimulator to emit the stimulation signal comprises:

causing the stimulator to emit the stimulation signal embodied as one of: an electrical pulse, a vibration, or a heat signal.

15. The system of claim 10, wherein the stimulation parameters comprise one or more of: an intensity level, a pulse width, and a pulse duration.

16. The system of claim 10, wherein determining splinting occurrence comprises:

comparing, using a machine learning model, the breathing waveform data to the expected breathing waveform.

17. The system of claim 10, wherein causing the stimulator configured to be in contact with the monitored individual to emit the stimulation signal to the monitored individual comprises:

causing the stimulator to emit the stimulation signal to a region of the monitored individual.

18. One or more non-transitory computer-readable storage media including instructions that, when executed by one or more processors, cause the one or more processors to:

receive breathing pattern sensory data generated based at least in part on output of a breathing sensor monitoring a breathing of a monitored individual;

generate breathing waveform data reflecting a breathing cycle of the monitored individual comprising an actual inspiration portion and an actual expiration portion, based at least in part on the breathing pattern sensory data for the monitored individual;

determine a splinting occurrence reflected within the breathing waveform data, wherein:

(i) the splinting occurrence is defined by a shortened inspiration portion of the breathing cycle relative to an expected inspiration portion of an expected breathing waveform for the monitored individual, and (ii) the shortened inspiration portion of the breathing cycle is determined based on a difference measure between (a) a measured time between an actual start of the actual inspiration portion and an actual peak of the actual inspiration portion and (b) an expected time between an expected start of the expected inspiration portion and an expected peak of the expected inspiration portion;

in response to the splinting occurrence, map a stimulation schedule to the breathing waveform data, wherein the stimulation schedule defines a plurality of stimulation triggers reflected within the breathing waveform data and detectable within the breathing pattern sensory data for stimulating nerves of the monitored individual; and in response to detecting a stimulation trigger of the plurality of stimulation triggers within the breathing pattern sensory data, cause a stimulator configured to be in contact with the monitored individual to emit a stimulation signal to the monitored individual, wherein the stimulation signal is characterized by stimulation parameters.

19. The one or more non-transitory computer-readable storage media of claim 18, wherein determining the splinting occurrence comprises identifying a location within the breathing waveform data reflecting a difference between the breathing waveform data and the expected breathing waveform.

20. The one or more non-transitory computer-readable storage media of claim 18, wherein (i) the splinting occurrence is associated with an occurrence timestamp and (ii) the stimulation trigger is associated with an emit timestamp that is temporally aligned with the occurrence timestamp.

* * * * *